United States Patent
Alezra et al.

(10) Patent No.: US 9,711,253 B2
(45) Date of Patent: Jul. 18, 2017

(54) METHOD AND SYSTEM FOR ELECTRON RADIOTHERAPY

(75) Inventors: Dror Alezra, Rishon-LeZion (IL); Eran Nardi, Ramat-Efal (IL); Sion Koren, Philadelphia, PA (US); Itzhak Orion, LeHavim (IL)

(73) Assignees: Tel HaShomer Medical Research Infrastructure and Services Ltd., Ramat-Gan (IL); Ben-Gurion University of the Negev Research and Development Authority, Beer-Sheva (IL)

(*) Notice: Subject to any disclaimer, the term of this patent is extended or adjusted under 35 U.S.C. 154(b) by 0 days.

(21) Appl. No.: 13/989,806

(22) PCT Filed: Nov. 28, 2011

(86) PCT No.: PCT/IL2011/050033
§ 371 (c)(1),
(2), (4) Date: May 27, 2013

(87) PCT Pub. No.: WO2012/070054
PCT Pub. Date: May 31, 2012

(65) Prior Publication Data
US 2013/0259198 A1     Oct. 3, 2013

Related U.S. Application Data
(60) Provisional application No. 61/417,434, filed on Nov. 28, 2010.

(51) Int. Cl.
G21K 1/093     (2006.01)
A61N 5/10      (2006.01)
A61B 5/05      (2006.01)

(52) U.S. Cl.
CPC .......... G21K 1/093 (2013.01); A61B 5/05 (2013.01); A61N 5/1042 (2013.01); A61N 5/1043 (2013.01); A61N 2005/1089 (2013.01)

(58) Field of Classification Search
CPC .......... A61N 2005/1089; A61N 5/1048; G01R 33/381; G01R 33/385; G21K 1/093; G21K 5/00; H01J 37/1475
(Continued)

(56) References Cited

U.S. PATENT DOCUMENTS 4,134,017 A     1/1979  Azam et al.
5,317,164 A *   5/1994  Kurokawa .................. 250/492.3
(Continued)

FOREIGN PATENT DOCUMENTS

JP     2010167137 A *  8/2010  ............... A61N 5/10
WO   WO 2011050822 A1 *  5/2011  ............... A61N 5/10
WO   WO 2012/070054       5/2012

OTHER PUBLICATIONS

Becchetti et al., "Magnetic confinement of Radiotherapy beam-dose profiles", Cyclotrons and their applications, 2001.*
(Continued)

*Primary Examiner* — Michael Logie

(57) ABSTRACT

A radiotherapy system is disclosed. The radiotherapy system comprises an electron beam generator for generating an electron beam and a magnetic field generator for generating a magnetic field. In some embodiments of the present invention, the system further comprises a controller for controlling the electron beam and the magnetic field generators such that the electron beam is dynamically shifted and the magnetic field is dynamically redirected synchronously with the shifting.

19 Claims, 31 Drawing Sheets
(27 of 31 Drawing Sheet(s) Filed in Color)

(58) Field of Classification Search
USPC ............................. 250/492.3, 396 ML, 398
See application file for complete search history.

(56) References Cited

U.S. PATENT DOCUMENTS

| | | | | |
|---|---|---|---|---|
| 6,060,833 | A * | 5/2000 | Velazco | 315/5.41 |
| 7,375,357 | B2 * | 5/2008 | Kaufman | 250/492.3 |
| 7,835,492 | B1 | 11/2010 | Sahadevan | |
| 2001/0001807 | A1 * | 5/2001 | Green | 600/411 |
| 2004/0079899 | A1 * | 4/2004 | Ma | 250/492.3 |
| 2006/0049902 | A1 * | 3/2006 | Kaufman | 335/306 |
| 2008/0208036 | A1 * | 8/2008 | Amies et al. | 600/411 |
| 2010/0102244 | A1 * | 4/2010 | Zdasiuk et al. | 250/396 ML |
| 2011/0118588 | A1 * | 5/2011 | Komblau et al. | 600/411 |
| 2011/0213239 | A1 * | 9/2011 | Amies | A61N 5/1049 600/411 |
| 2011/0260729 | A1 * | 10/2011 | Carlone | G01R 33/4812 324/318 |

OTHER PUBLICATIONS

Shih, "High energy electron radiotherapy in a magnetic field", Medical Physics, 1975.*

Glinec et al. "Radiotherapy with laser-plasma accelerators: Monte Carlo simulation of dose deposited by an experimental quasimonoenergetic electron beam", Medical physics, 2006.*

Communication Relating to the Results of the Partial International Search Dated Mar. 14, 2012 From the International Searching Authority Re. Application No. PCT/IL2011/050033.

International Search Report and the Written Opinion Dated Apr. 25, 2012 From the International Searching Authority Re. Application No. PCT/IL2011/050033.

Becchetti et al. "High Energy Electron Beams Shaped With Applied Magnetic Fields Could Provide A Competitive and Cost-Effective Alternative to Proton and Heavy-Ion Radiotherapy", Medical Physics, XP012011633, 29(10): 2435-2437, Oct. 1, 2002.

Nardi et al. "Electron Beam Therapy With Coil-Generated Magnetic Fields", Medical Physics, XP012074922, 31(6): 1494-1503, Jun. 1, 2004.

International Preliminary Report on Patentability Dated Jun. 6, 2013 From the International Bureau of WIPO Re. Application No. PCT/IL2011/050033.

Communication Pursuant to Article 94(3) EPC Dated Mar. 5, 2015 From the European Patent Office Re. Application No. 11808367.4.

Office Action Dated Aug. 16, 2016 From the Israel Patent Office Re. Application No. 226594 and Its Translation Into English.

* cited by examiner

METHOD AND SYSTEM FOR ELECTRON RADIOTHERAPY

RELATED APPLICATIONS

This application is a National Phase of PCT Patent Application No. PCT/IL2011/050033 having International filing date of Nov. 28, 2011, which claims the benefit of priority under 35 USC §119(e) of U.S. Provisional Patent Application No. 61/417,434, filed on Nov. 28, 2010. The contents of the above applications are all incorporated by reference as if fully set forth herein in their entirety.

FIELD AND BACKGROUND OF THE INVENTION

The present invention, in some embodiments thereof, relates to radiation therapy and, more particularly, but not exclusively, to electron radiotherapy.

Radiation has long been used to treat a variety of cancers by delivering a high local dose of radiation directly to the tumor bed through the operative site. Early radiation treatment methods utilized X-rays as the radiation source. More recent therapy installations have employed beams of high energy electrons as the radiation source to provide a homogeneous dose of radiation with a rapid falloff in radiation intensity beyond the treatment volume, thereby minimizing exposure of non-cancerous tissue to the radiation.

A conventional electron radiotherapy system generally includes a linear electron beam accelerator which accelerates electron to high energy. The high energy electron beam emerging from the accelerator is further processed to produce an electron beam suitable for patient treatment. The patient is placed on a treatment couch that can be precisely positioned to locate the treatment region, which is usually a cancerous tumor or lesion in the patient.

There is generally a difficulty to focus the radiotherapy beam with sufficient precision on the target location. Current medical practice is, therefore, to increase the irradiated area to include additional tissue volume and to increase the dosage of the radiotherapy beam to ensure complete cell death in the target location. The expectation is that all cells in the treated region are killed and possible positioning errors between the beam and the region are compensated. However, such techniques inevitably cause increased collateral radiation damage to the volume abutting the desired region to be treated, in some cases resulting in devastating quality of life effects on the subject.

Known in the art is an electron radiotherapy technique in which a transverse magnetic field is introduced at the target region so as to cause the electrons to spiral in this region and to produce an effective peak in the depth-dose distribution within the tumor volume, thereby to improve the therapeutic dose distribution [Nardi E and Barnea G (1999), Med. Phys. 26(6):967; Nardi et al. (2004), Med. Phys. 31(6):1494; Becchetti ED and Sisterson J M (2002), Med. Phys. 29(10): 2435].

U.S. Pat. No. 4,868,843 discloses a radiotherapy system which produces irregular X-ray radiation field shapes so as to shield critical organs not invaded by the tumor. The system includes a multileaf collimator formed of a multiplicity of heavy to metal bar leaves driven relative to a pair of frames which are driven relative to jaws of a rectangular field collimator. A multiplicity of compensators, one attached to each leaf on one of the pair of frames is used to adjust the local intensity of the X-ray radiation within the field. The X-ray beam is limited to a fan with the jaws, the ends and selected parts of the fan are blocked by the multileaf collimator, and the intensity within various portions of the remaining beam is adjusted with compensators. The field of the fan beam is dynamically controlled by these means while the patient table is moved perpendicular to the plane of the fan beam.

Additional background art includes: Bielajew, A. F., "Electron Transport in E and B Fields" in Monte Carlo Transport of Electrons and Photons," W. R. N. T. E. Jenkins, A. Rindi, A, E. Nahum, and D. W. O. Rogers, editor (1987), Plenum Press, New York. 421-434; and Becchetti, F. D., J. M. Sisterson, W. R. Hendee, and Moderator, "High energy electron beams shaped with applied magnetic fields could provide a competitive and cost-effective alternative to proton and heavy-ion radiotherapy," (2002) Medical Physics 29:2435-2437.

SUMMARY OF THE INVENTION

Aspects of some embodiments of the present invention provide a system and method for radiotherapy. The system and method are capable of providing a predetermined energy dose to a predetermined target-region within a living body during electron radiotherapy. The target-region is preferably internal, i.e., non-superficial. The system and method of the present embodiments apply a magnetic field such as to control the spatial distribution of the electrons in an electron beam.

The therapeutic efficiency induced by the method and system of the present embodiments is at least the same as the therapeutic efficiency induced by ion beam therapy techniques. The advantage of the present embodiments is that the system is considerably less expensive than ion beam therapy systems and can be employed in many medical institutes, particularly medical institutes with limited budget.

Some embodiments of the present invention can be employed as add-ons for existing electron beam systems. These embodiments are particularly useful for medical institutes which are already in possession of electron beam systems, e.g., for the treatment of superficial tumors. The medical institute can therefore employ the to technique of the present embodiments without the need to purchase a new therapy system.

The radiotherapy system of the present embodiments generally comprises an electron beam generator and a magnetic field generator. In some embodiments of the present invention system further comprises a controller for controlling the electron beam and the magnetic field generators such that the electron beam is dynamically shifted and the magnetic field is dynamically redirected synchronously with the shifting. In some embodiments of the present invention the magnetic field is a multiple dipoles magnetic field. In some embodiments of the present invention a multileaf collimator is used, for example, for shifting the electron beam.

Hence, according to an aspect of some embodiments of the present invention there is provided a radiotherapy system. The system comprises an electron beam generator for generating an electron beam; a magnetic field generator for generating a magnetic field; and a controller for controlling the electron beam and the magnetic field generators, such that the electron beam is dynamically shifted and the magnetic field is dynamically redirected synchronously with the shifting.

According to some embodiments of the present invention the shifting and the redirecting is done such as to deliver a sufficiently high energy-dose to a sufficiently small internal target location in a living body.

According to an aspect of some embodiments of the present invention there is provided a radiotherapy system. The system comprises an electron beam generator for generating an electron beam; and a magnetic field generator for generating a magnetic field. In various exemplary embodiments of the invention, the magnetic field is a multiple dipoles magnetic field, such as, but not limited to, a quadrupole magnetic field, a hexapole magnetic field and an octupole magnetic field.

According to an aspect of some embodiments of the present invention there is provided a radiotherapy system. The system comprises an electron beam generator for generating an electron beam, and a magnetic field generator for generating a magnetic field. In various exemplary embodiments of the invention the magnetic field generator comprises a strips multileaf collimator for generating magnetic fields in least two opposing directions.

According an aspect of some embodiments of the invention there is provided a method of radiotherapy. The method comprises directing an electron beam to a surface of a living body, generating a magnetic field within the living body, and dynamically shifting the electron beam and, synchronously with the shifting, dynamically redirecting the magnetic field.

According to an aspect of some embodiments of the present invention there is provided a radiotherapy method. The method comprises operating the system described herein, preferably using at least some of the parameters described herein.

According to some embodiments of the present invention a strength of the magnetic field and a cross-sectional area of the beam are selected sufficiently high such as to deliver a sufficiently high energy-dose to a sufficiently small internal target location in a living body.

According to some embodiments of the present invention the sufficiently high energy-dose is higher by at least X percents from an energy-dose delivered by the beam to a surface of the living body upon entry thereto, where X equals 50 or 60 or 70 or more.

According to some embodiments of the present invention the sufficiently small internal target location is located at least Z centimeters below a surface of the living body, where Z equals 5 or 6 or 7 or 8 or 9 or 10 or 11 or 12 or more.

According to some embodiments of the present invention the sufficiently small internal target location is at most 50 or at most 40 or at most 30 cubic centimeters or any other volume.

According to some embodiments of the present invention the beam has a cross-sectional area of at least 15 or at least 20 or at least 25 square centimeters, e.g., a pencil beam up to 40×40 cm.

According to some embodiments of the present invention the beam is at energy of at least 40 MeV or at least 50 MeV or at least 60 MeV or 10 to 150 MeV or more. The energy or any other parameter can be varied to get the desirable dose distribution.

According to some embodiments of the invention the magnetic field generator comprises two coils or magnets having a symmetry axis arranged to receive a living body therebetween such that symmetry axes of the coils or magnets do not intersect with the body.

According to some embodiments of the invention the magnetic field generator comprises two coils or magnets having a symmetry axis arranged to receive a living body therebetween such that symmetry axes of the coils or magnets intersect with the body.

According to some embodiments of the invention the magnetic field generator comprises four coils or magnets having a symmetry axis arranged to receive a living body such that a first pair of coils or magnets is at one side of the body and a second pair of coils or magnets is at an opposite side of the body, and wherein symmetry axes of the coils or magnets are at an angle to each other.

According to some embodiments of the invention the magnetic field generator comprises four coils or magnets having a symmetry axis arranged to receive a living body such that a first pair of coils or magnets is at one side of the body and a second pair of coils or magnets is at an opposite side of the body, and wherein symmetry axes of the coils or magnets intersect with the body.

According to some embodiments of the invention the magnetic field generator comprises four coils or magnets having a symmetry axis arranged to receive a living body such that the coils or magnets are distributed around the body, wherein symmetry axes of the coils or magnets intersect with the body.

According to some embodiments of the invention the magnetic field generator comprises six coils or magnets having a symmetry axis arranged to receive a living body such that a first triplet of coils or magnets is at one side of the body and a second triplet of coils or magnets is at an opposite side of the body, and wherein for each triplet, a symmetry axis of a middle coil or magnet of the triplet is generally orthogonal to symmetry axes of the other two coils or magnets of the triplet.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows magnetic field lines at a central cross section as generated by a Helmholtz coil system.

FIG. 2 shows results of simulations conducted for step-function magnetic field.

FIG. 3 shows the results of simulations performed using an EGS5 code system.

FIG. 4 shows electron trajectories without application of magnetic field.

FIG. 5 shows electron trajectories without application of magnetic field having step-function spatial dependence.

FIGS. 6A and 6B show results of simulations performed for a longitudinal magnetic field wherein the magnetic field is collinear with the electron beam.

FIG. 7 shows results of computer simulations for a 60 MeV parallel electron beam having, on entry, a square cross-sectional area of 1 cm$^2$, in the absence of magnetic field.

FIG. 8 shows results of computer simulations for a 60 MeV electron beam in the presence of a 3 T magnetic field directed along the y direction at z≥7 cm.

FIGS. 9A, 9B and 9C show results of computer simulations for a 60 MeV electron beam having, on entry, a square cross-sectional area of 25 cm$^2$, the presence of a 4 T magnetic field directed along the x direction at z≥10 cm.

FIG. 10A show simulation results of an electron beam shifted 5 cm in the x direction and magnetic field along the −y direction.

Figure 9A:
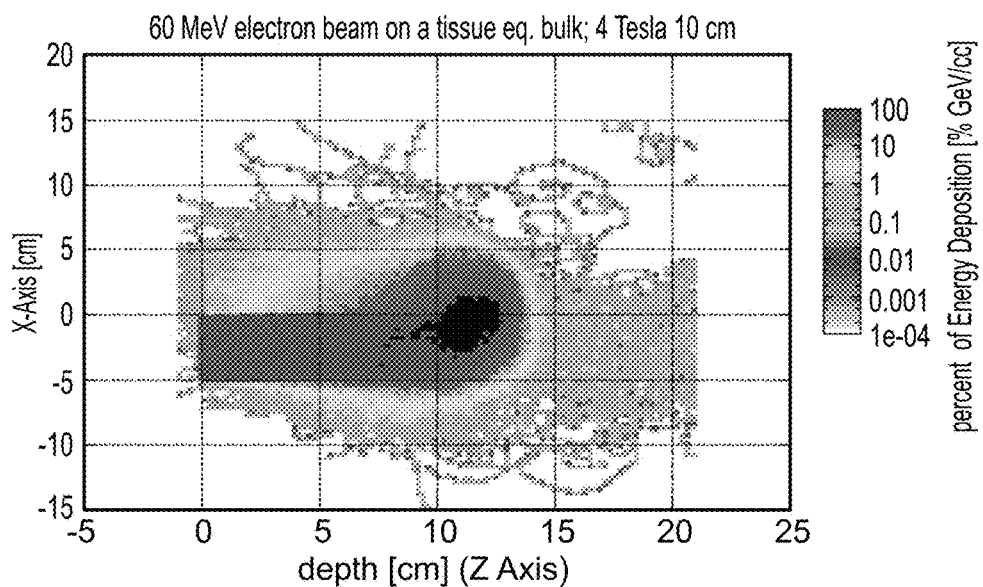
Figure 9B:
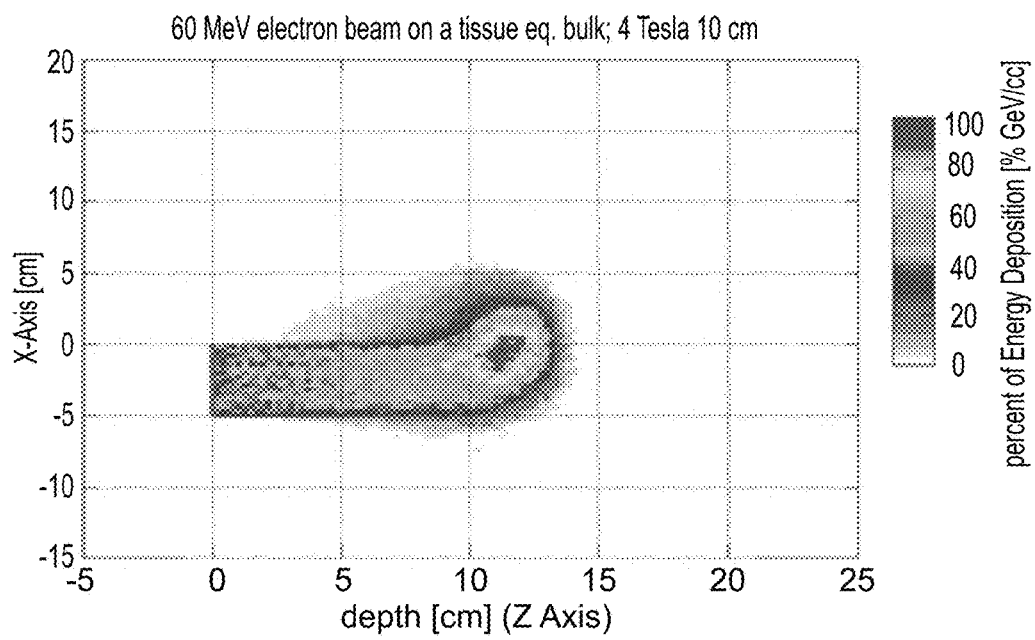
Figure 10A:
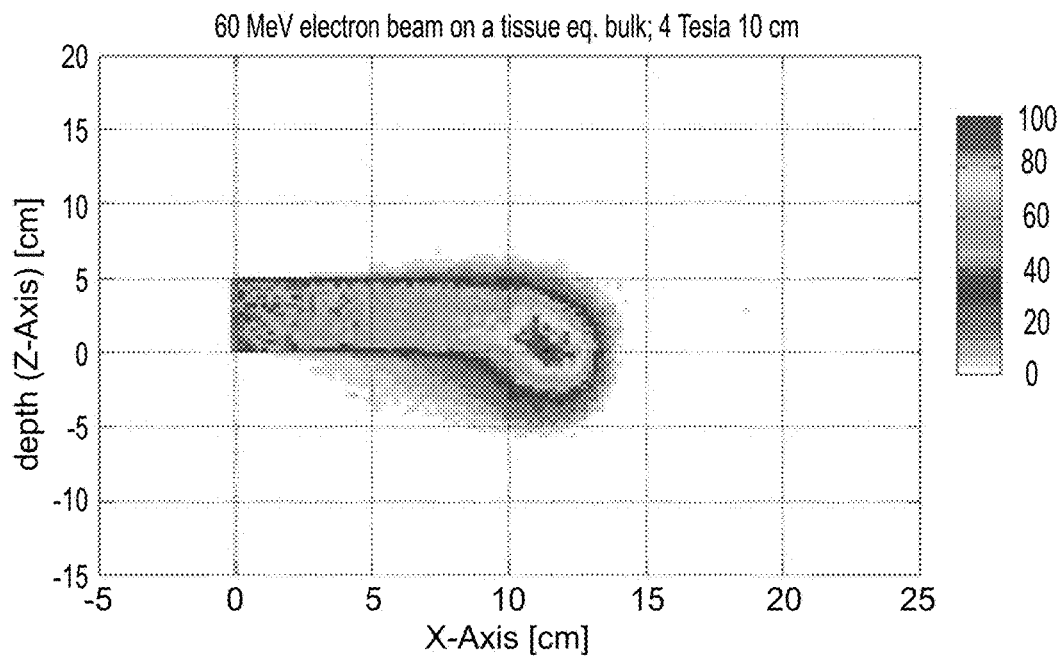
Figure 10B:
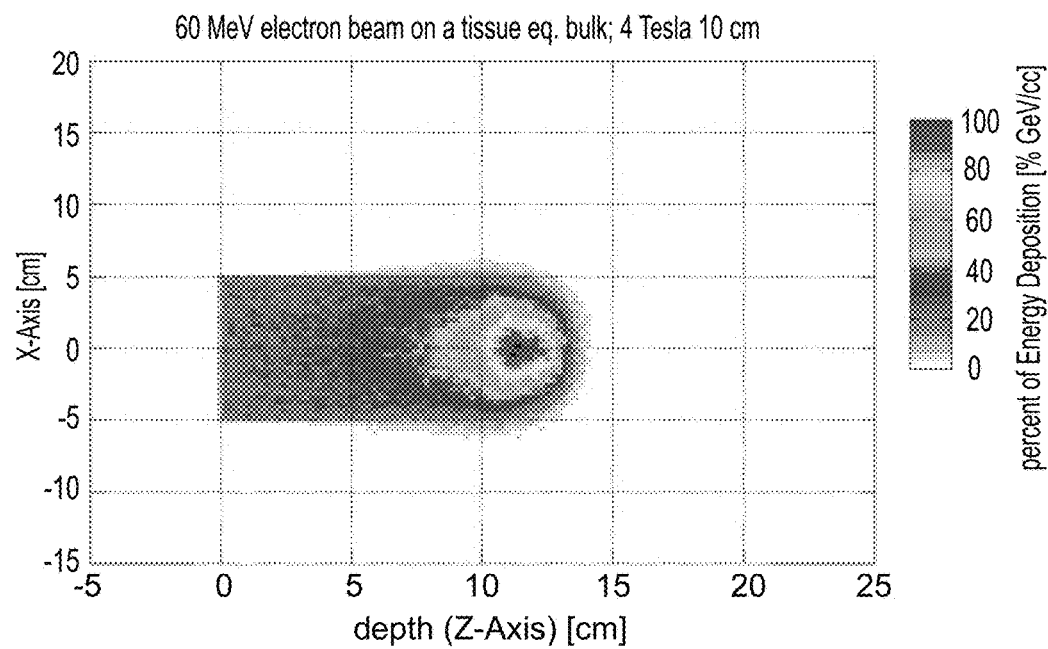
Figure 10C:
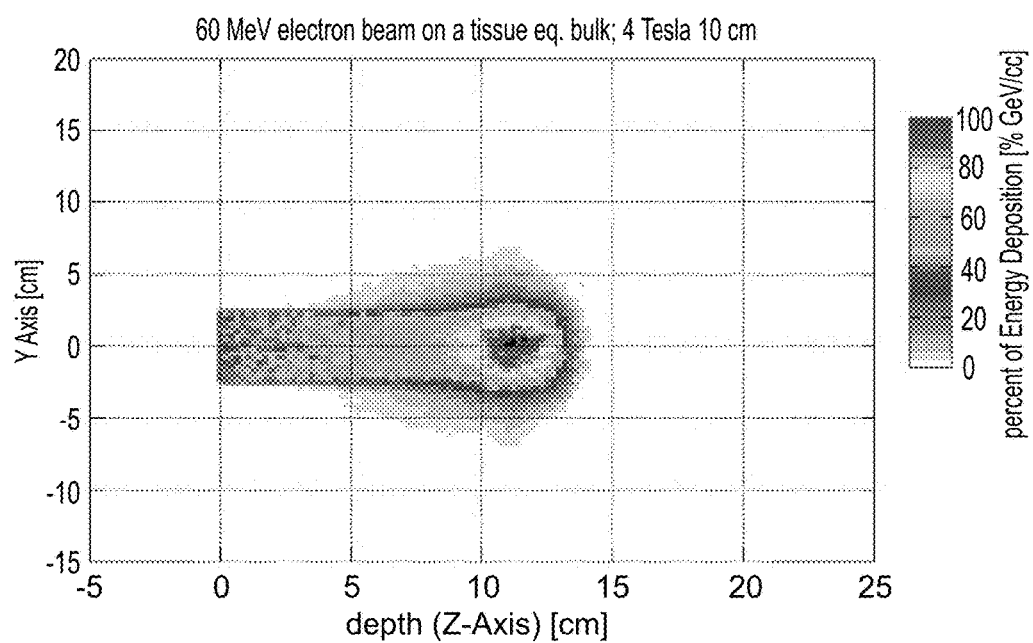
Figure 10D:
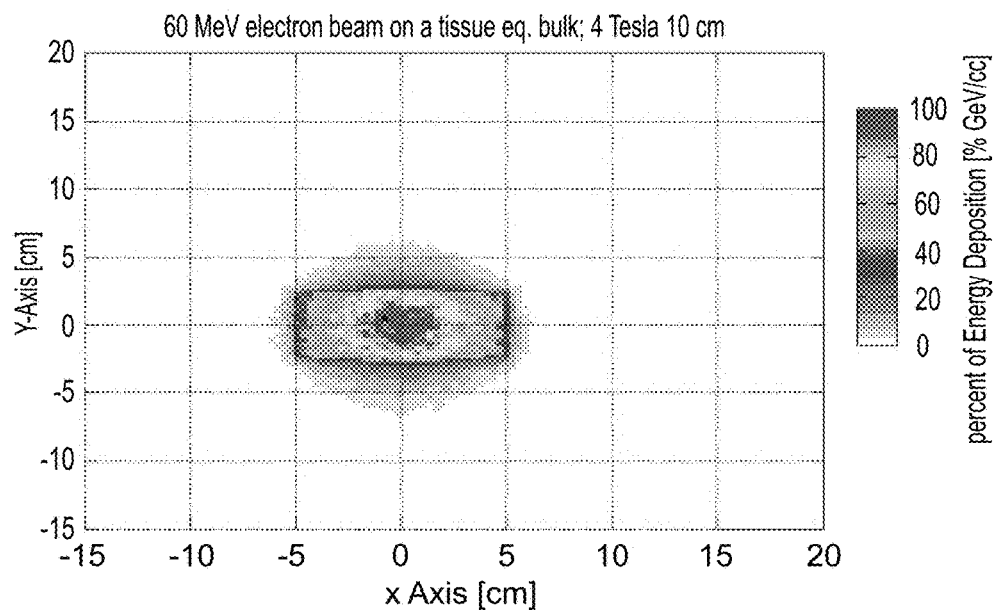

FIGS. 10B-D show the results of simulations which combine the simulations shown in FIGS. 9B and 10A.

Figure 11:
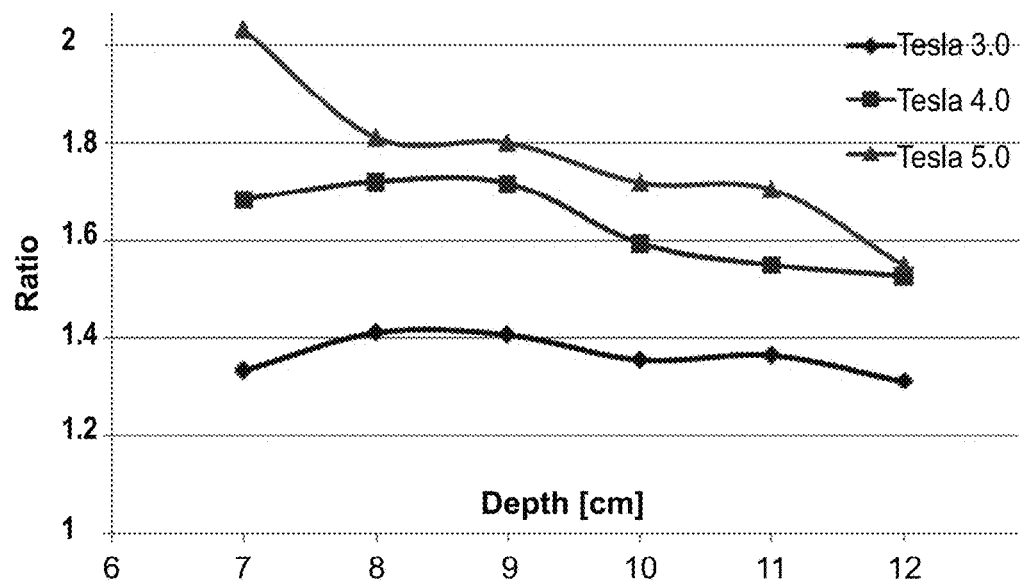

FIG. 11 is a graph describing the ratio of the maximal dose which is delivered with application of magnetic field to the maximal dose which is delivered in the absence of magnetic field.

Figure 12A:
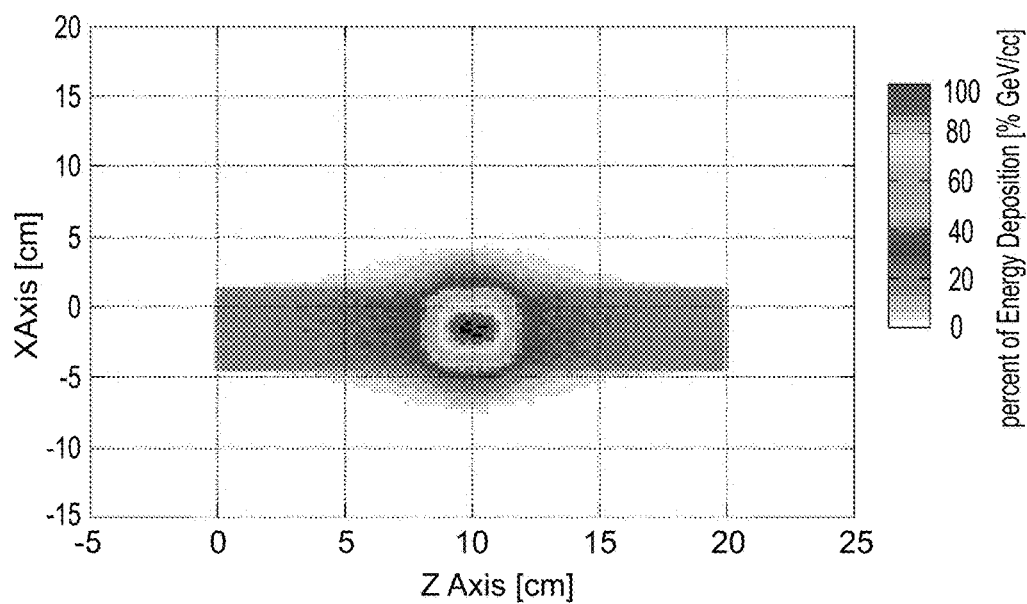
Figure 12B:
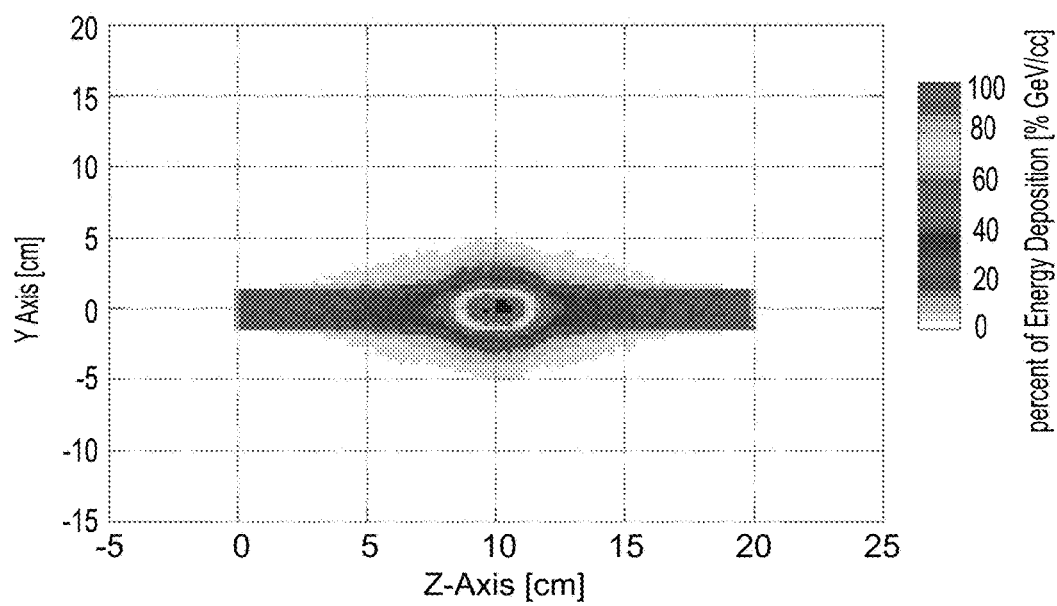
Figure 12C:
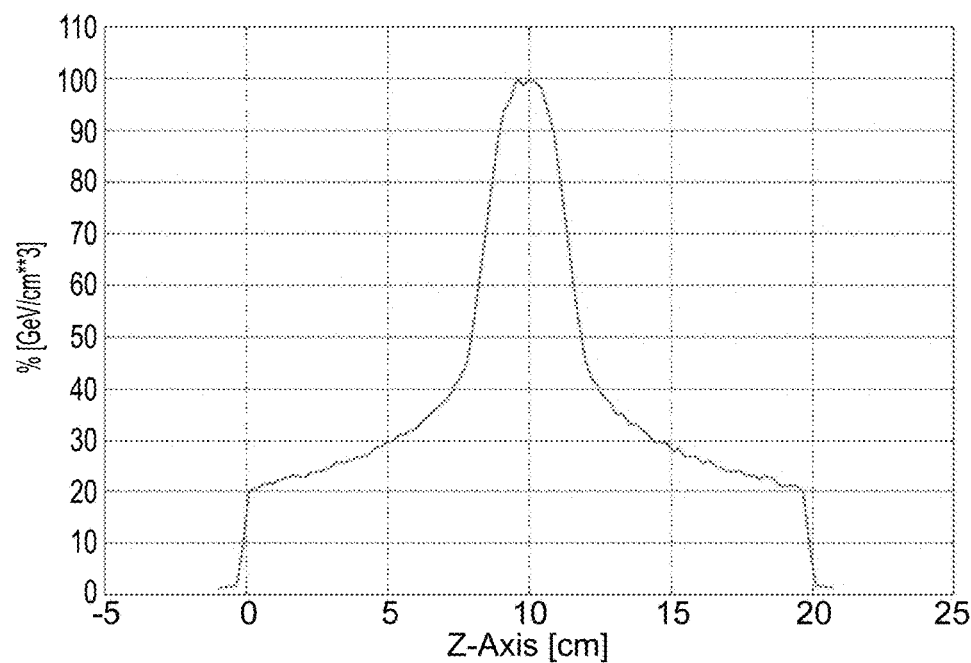

FIGS. 12A-C show simulation results for a 60 MeV two opposed electron beams with a magnetic field of 4 T at a target region located at a depth z of 10 cm.

FIGS. 13A-D show simulation results for a 60 MeV parallel electron beam propagating from z=−20 cm along the z direction and having, on entry, a square cross-sectional area of 40 cm$^2$, in the presence of a quadrupole magnetic field of 3.5 T applied at a target region located from z=−20 cm to z=+20 cm.

Figure 14:
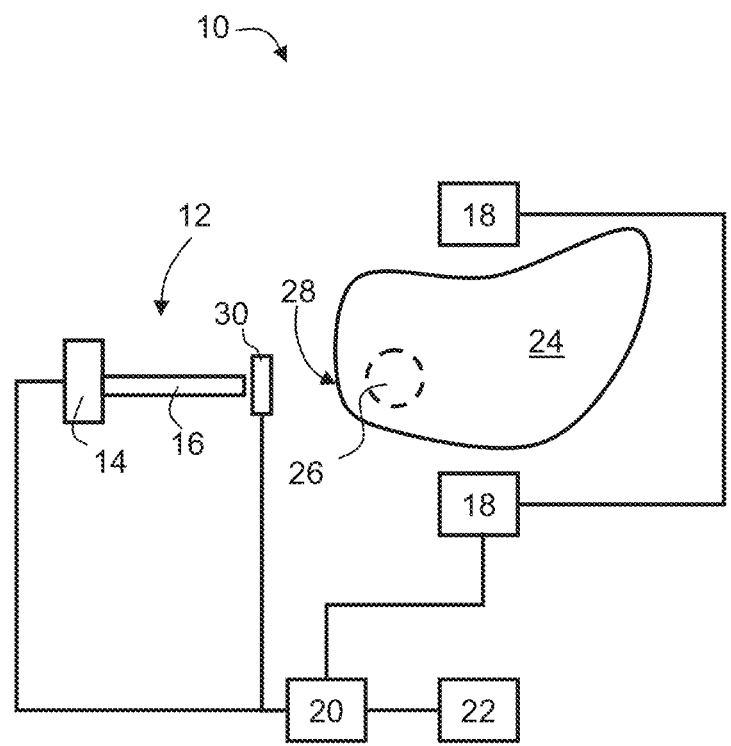

FIG. 14 is a schematic illustration of a radiotherapy system.

Figure 15:
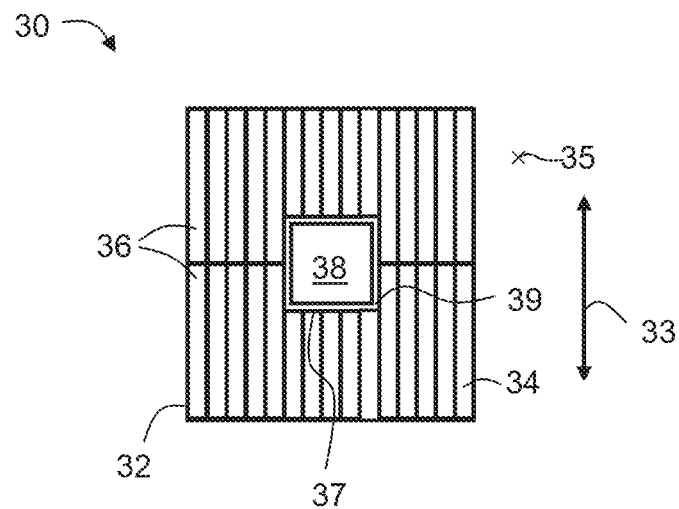

FIG. 15 is a schematic illustration of a multileaf collimator.

FIGS. 16A-G are schematic illustrations exemplifying various coil arrangements for a magnetic field generator.

FIGS. 17A-F shows magnetic field vectors and intensities for various coil arrangements for a magnetic field generator.

Figure 17A:
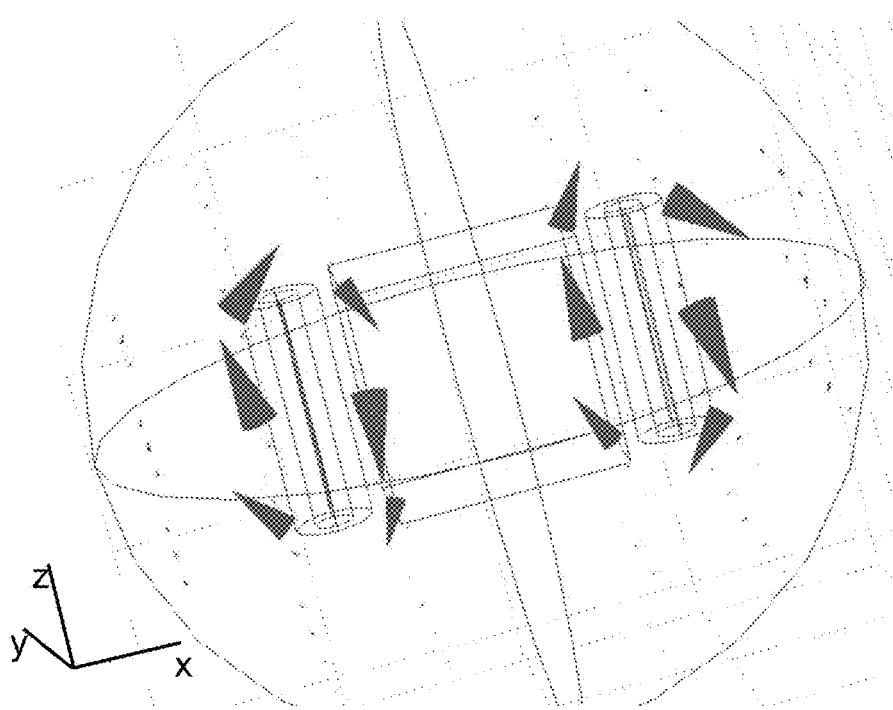
Figure 17B:
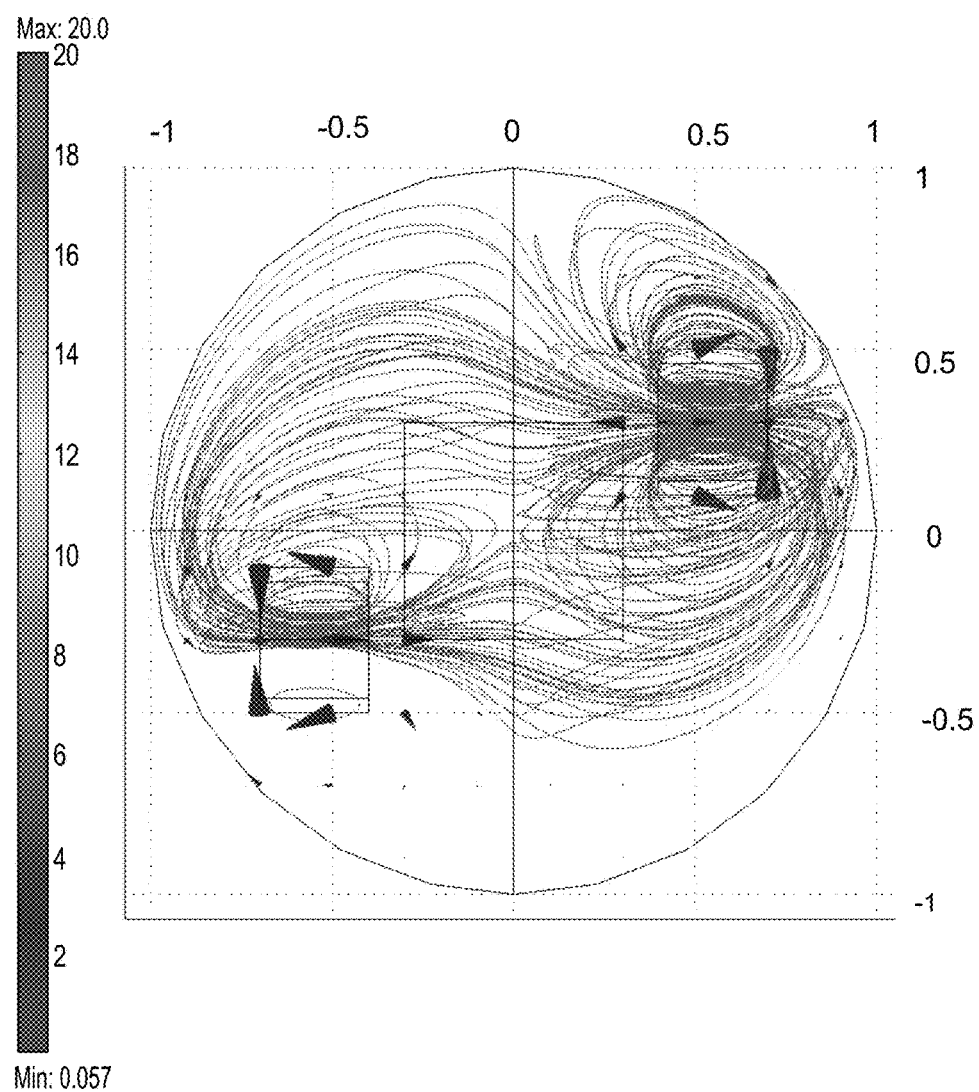
Figure 17C:
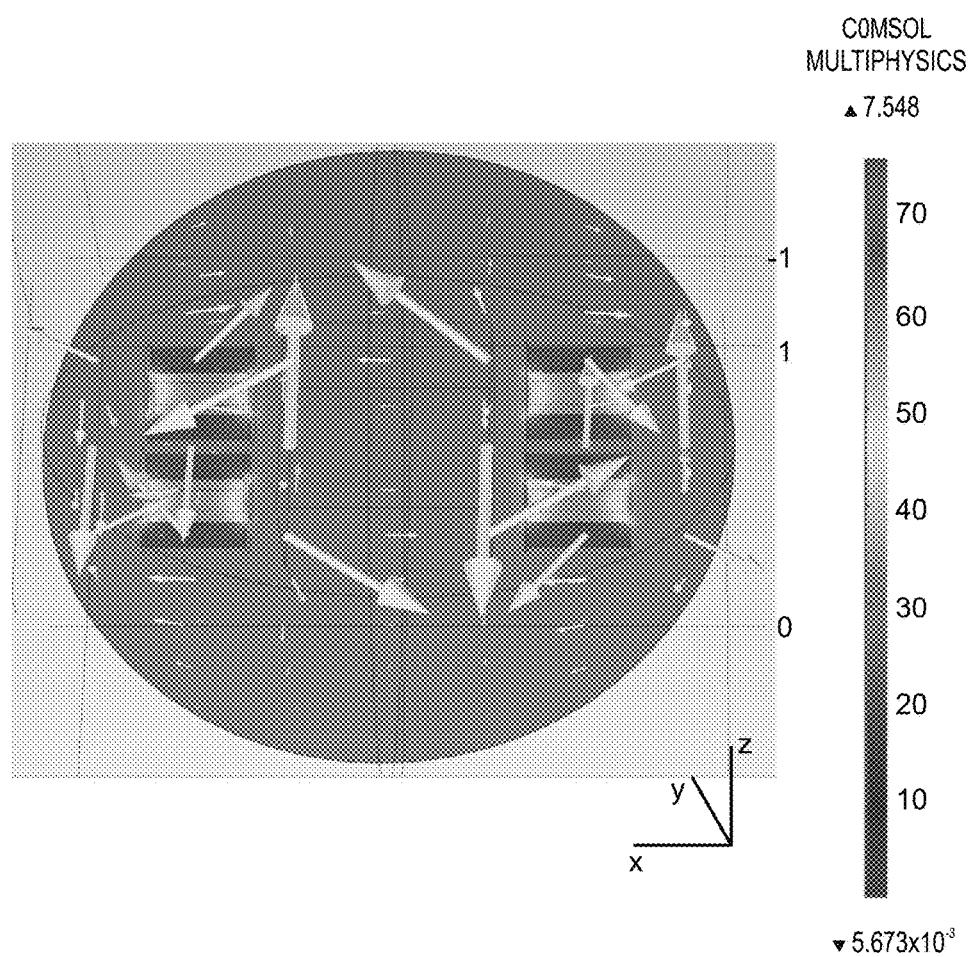
Figure 17D:
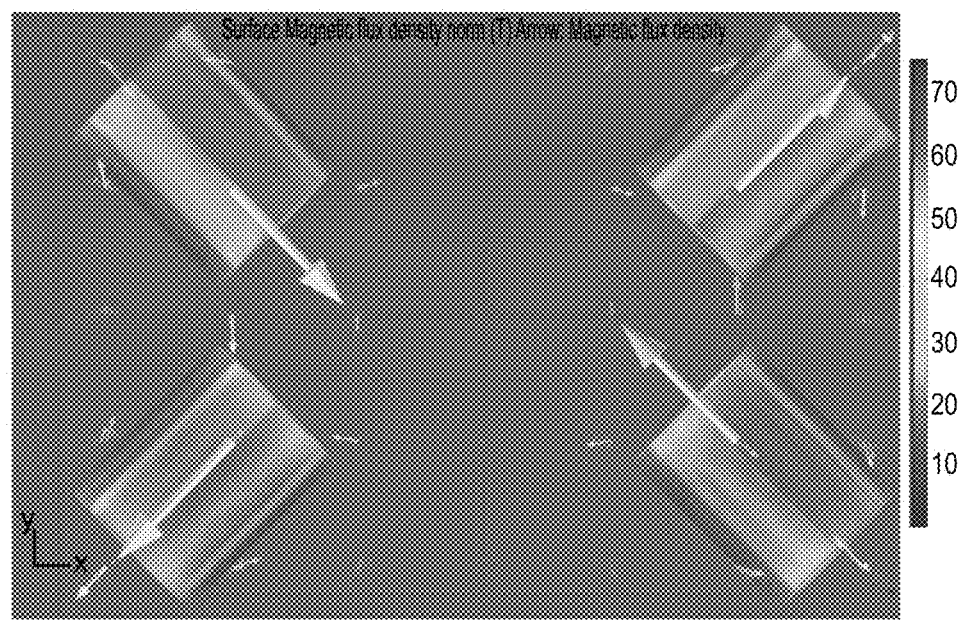
Figure 17E:
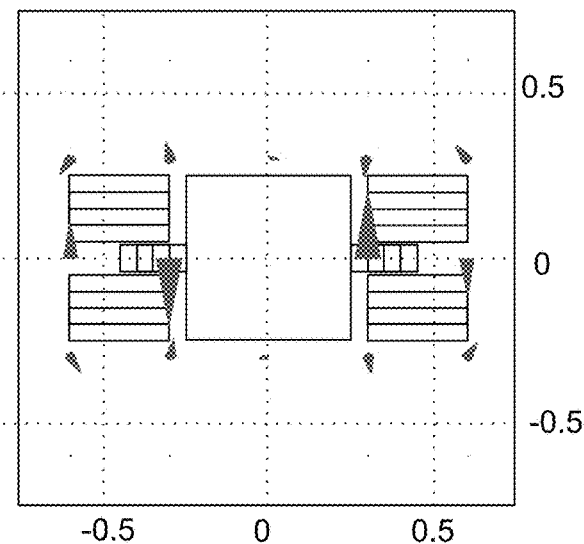
Figure 17F:
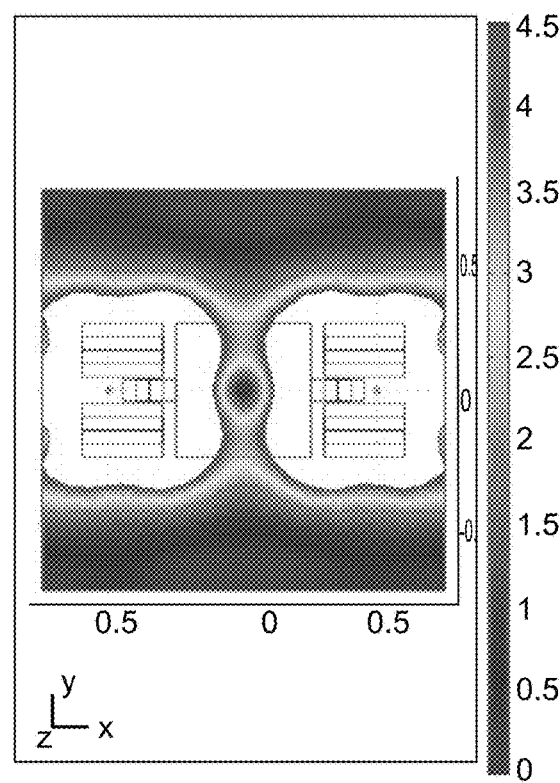
Figure 18A:
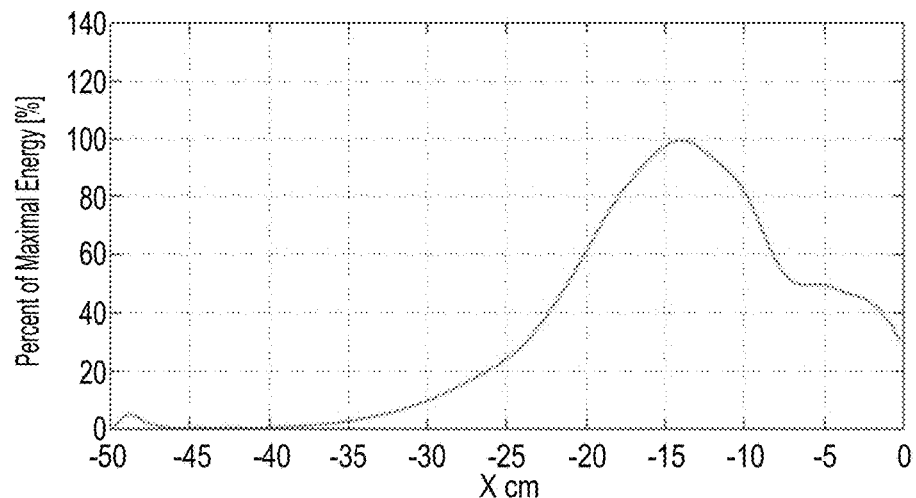
Figure 18B:
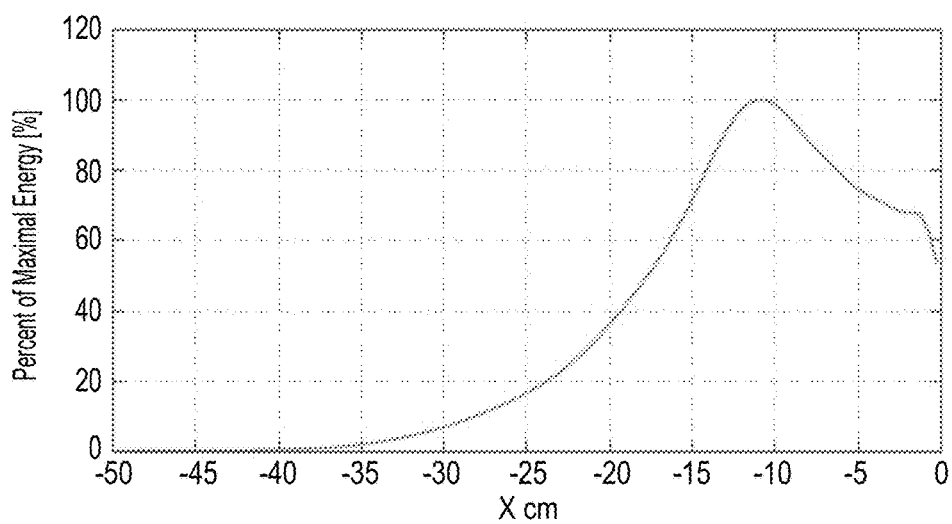
Figure 18C:
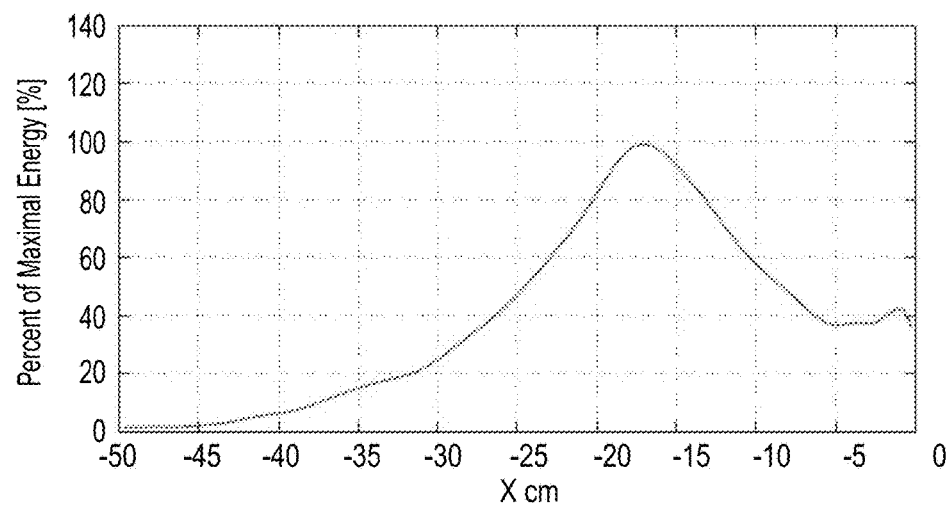
Figure 18D:
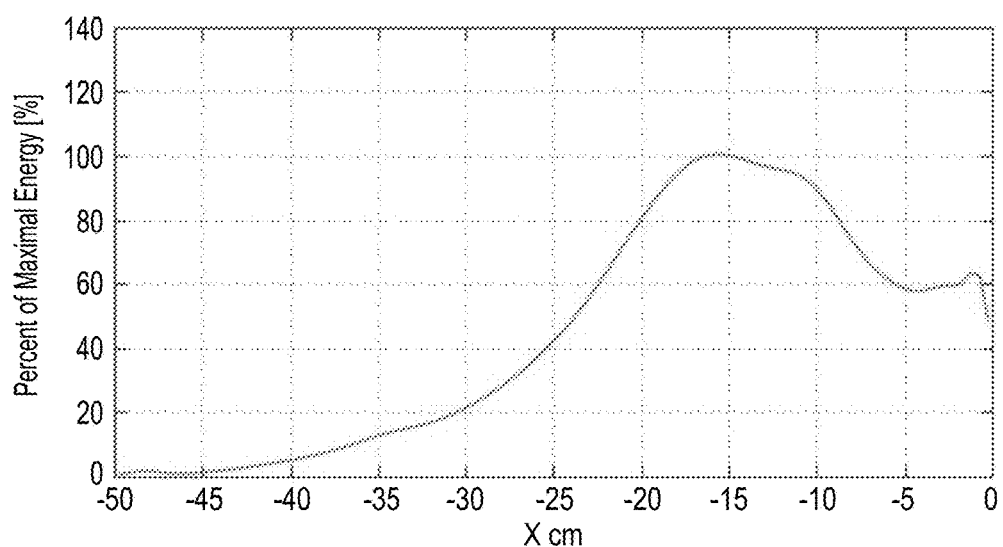
Figure 18E:
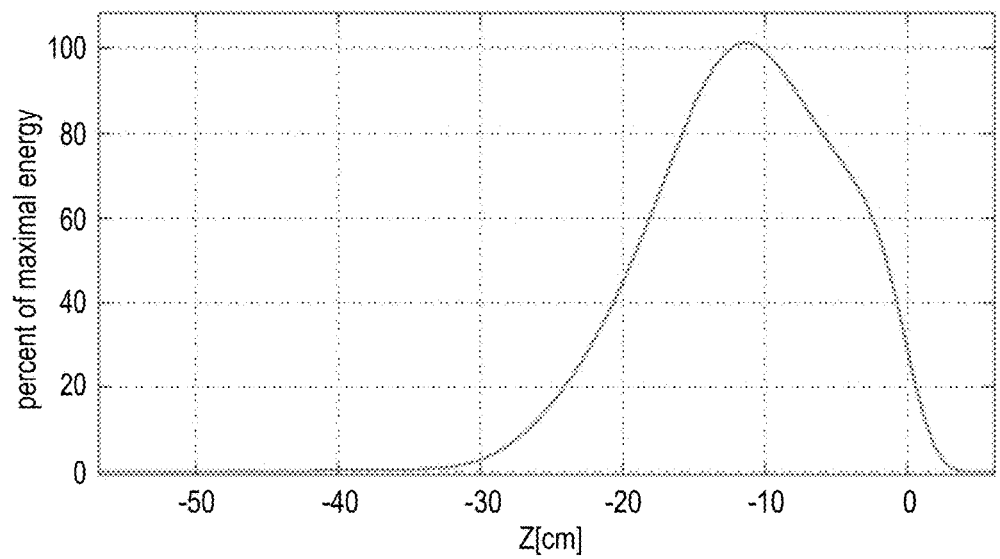
Figure 18F:
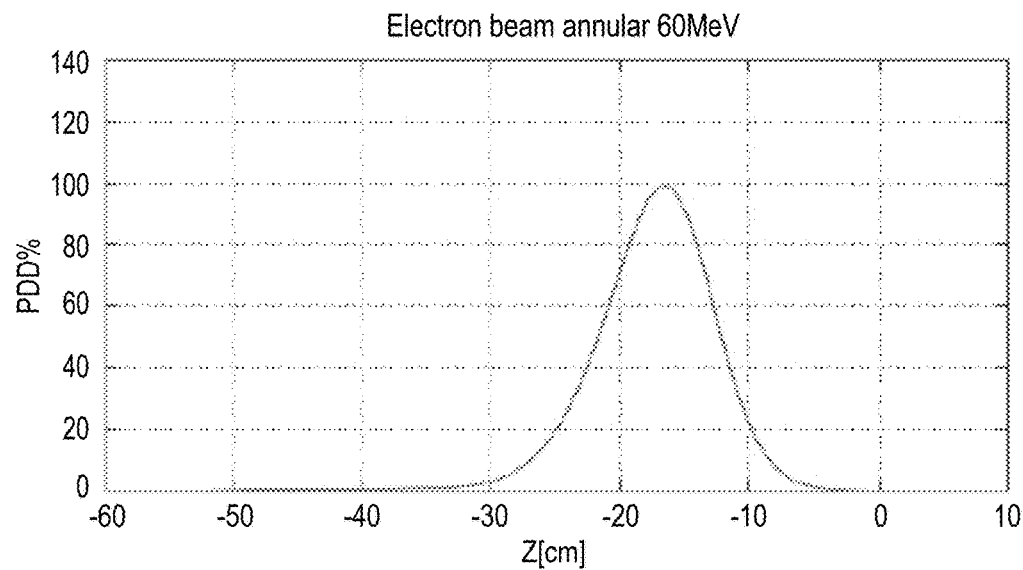
Figure 18G:
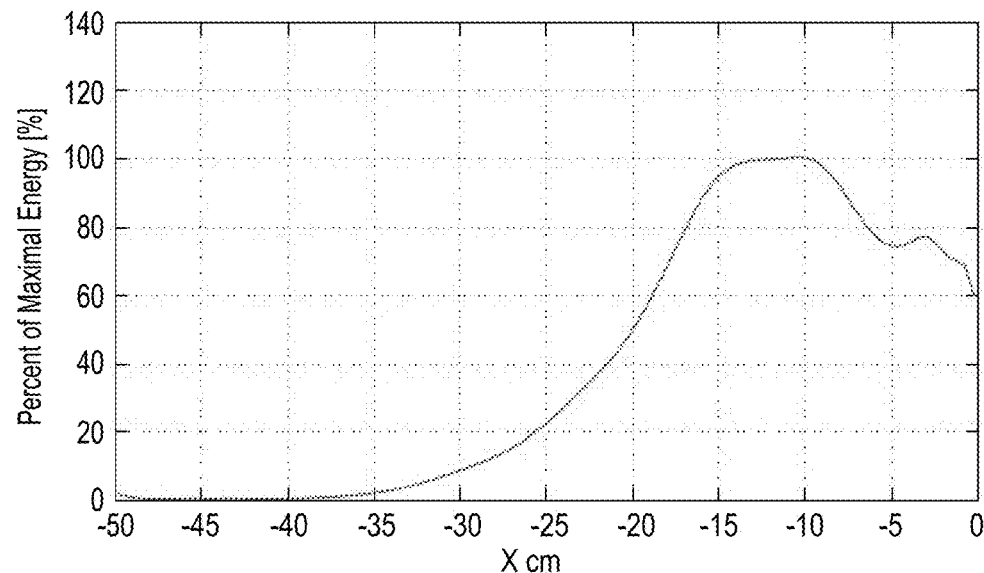
Figure 18H:
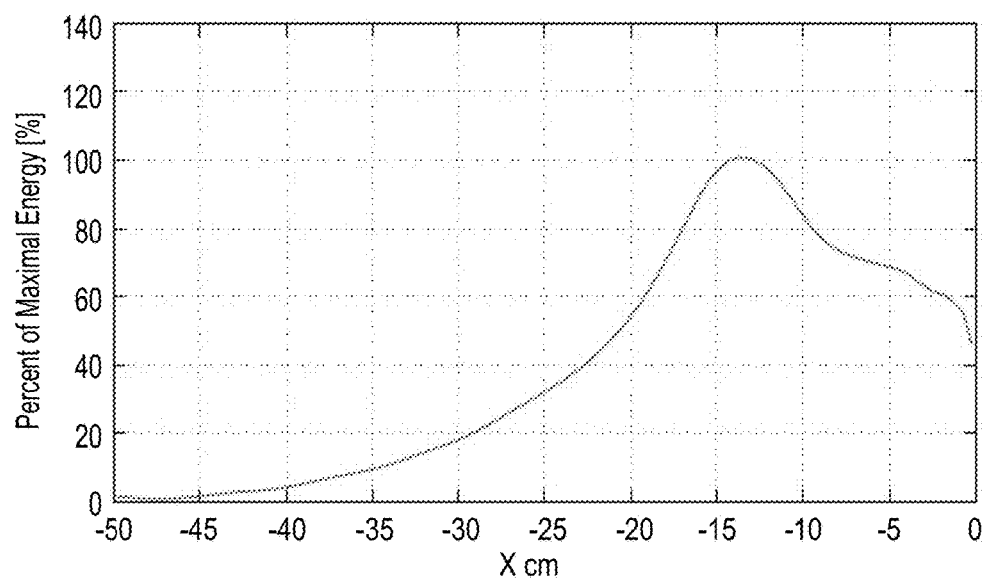
Figure 19A:
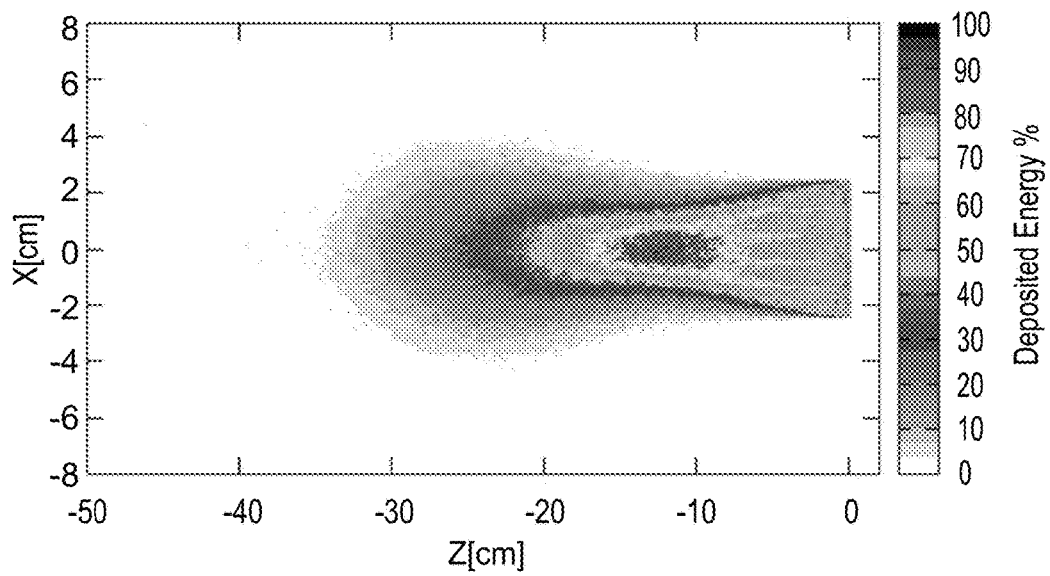
Figure 19B:
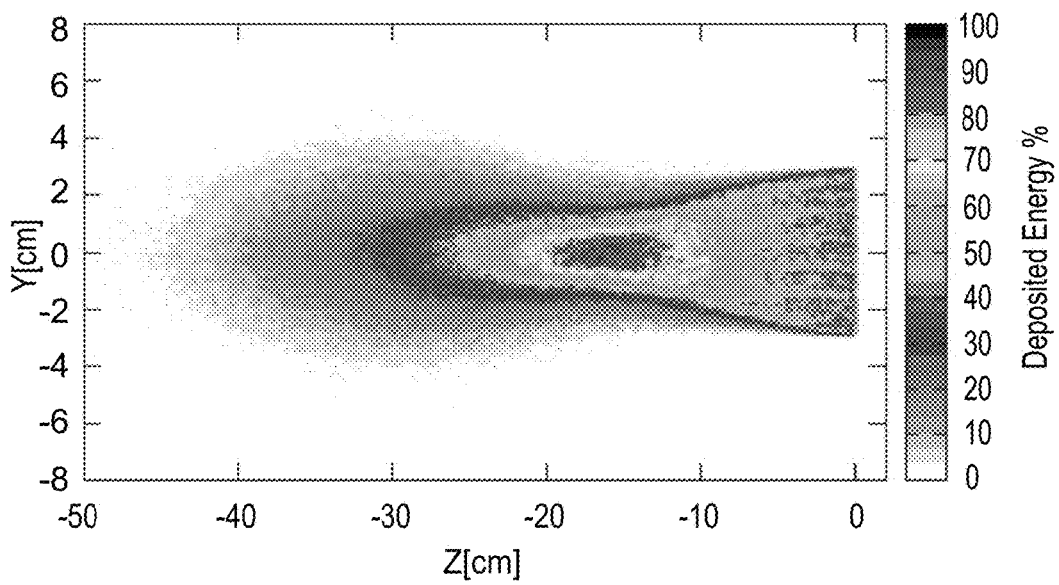
Figure 19C:
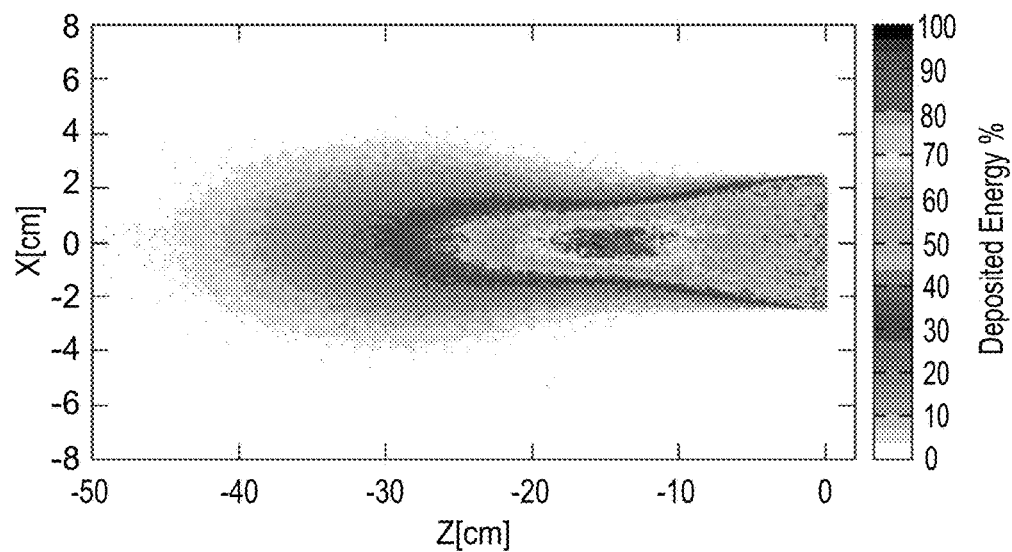
Figure 19D:
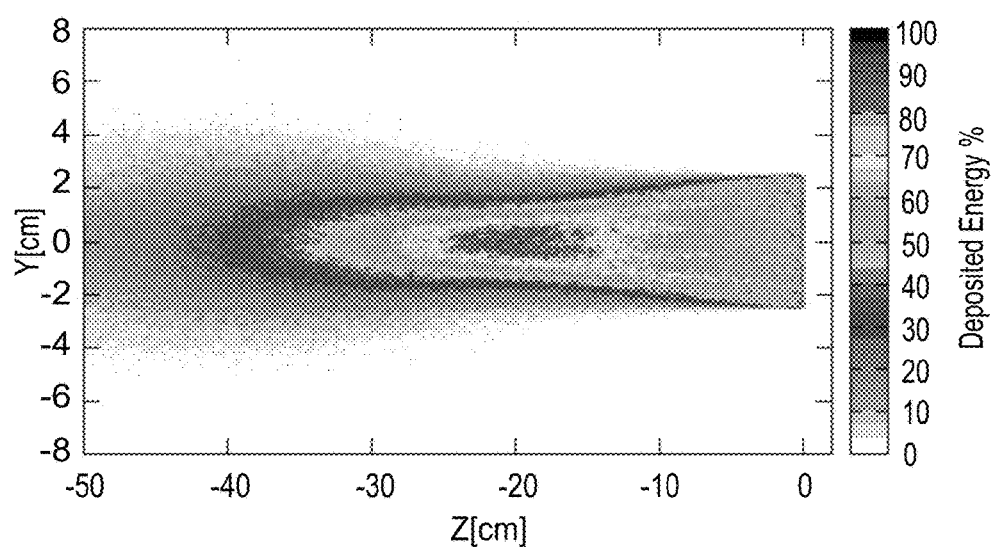
Figure 19E:
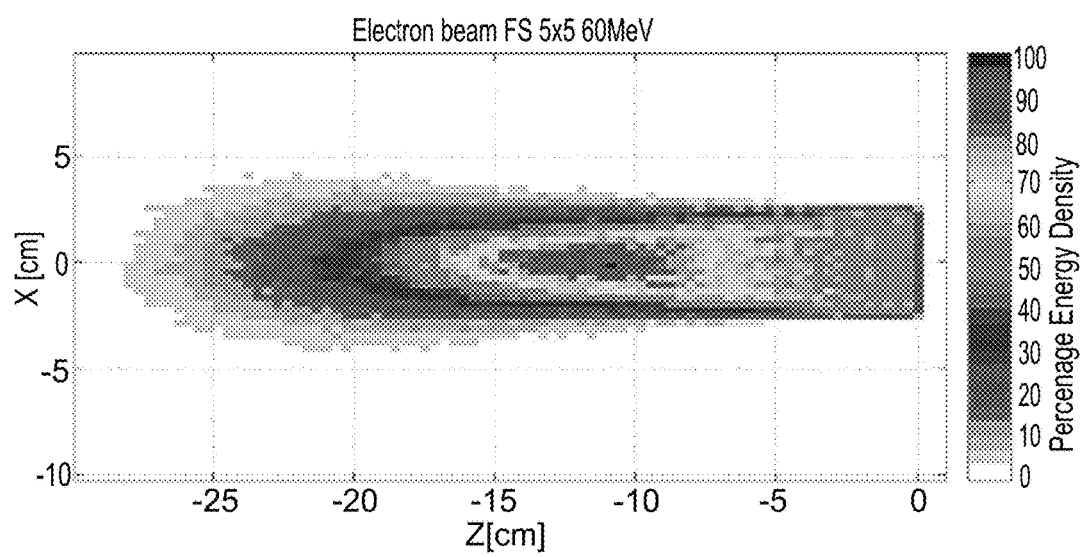
Figure 19F:
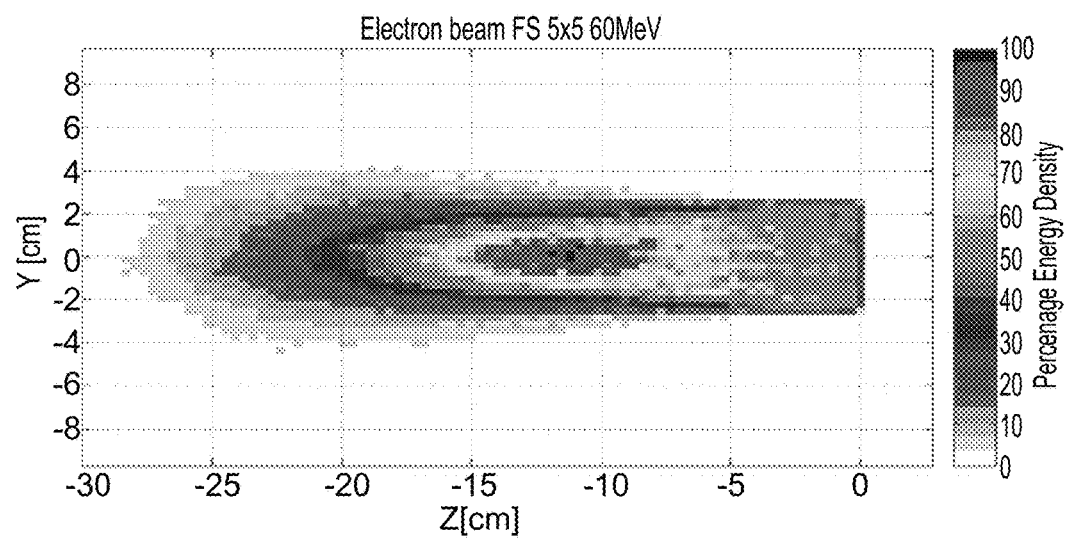
Figure 19G:
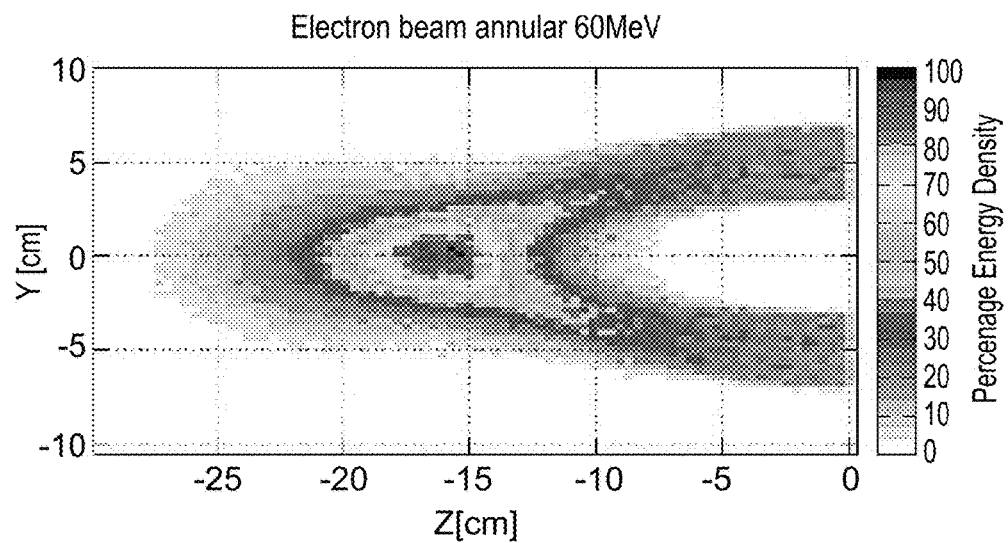
Figure 19H:
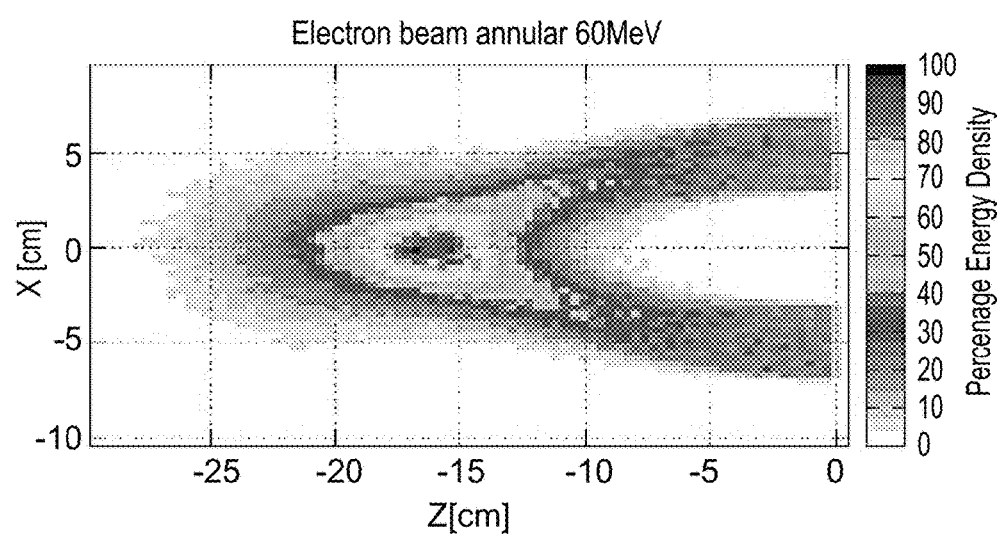

FIGS. 18A-H maximal energy in percentage as a function of the depth, as obtained by computer simulations performed for magnetic field generated by six coils arranged according to the configuration shown in FIGS. 17E and 17F.

FIGS. 19A-H show two-dimensional energy dose distributions, as obtained by computer simulations performed for magnetic field generated by six coils arranged according to the configuration shown in FIGS. 17E and 17F.

Figure 20A:
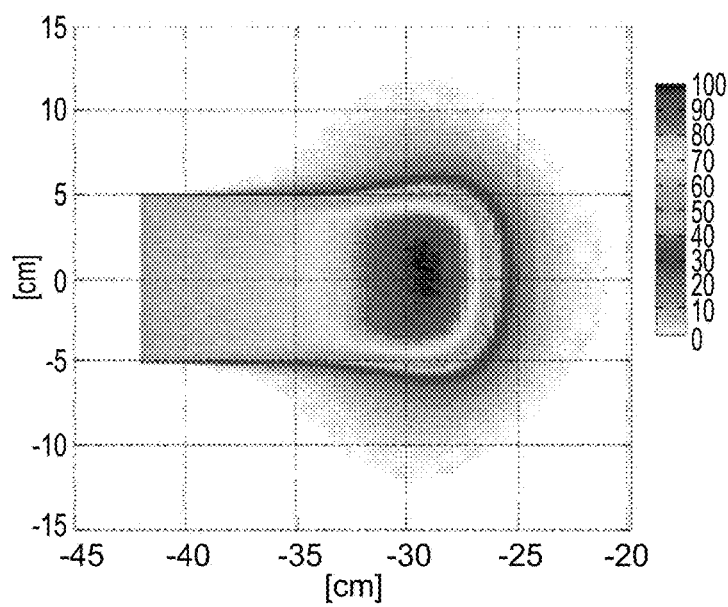
Figure 20B:
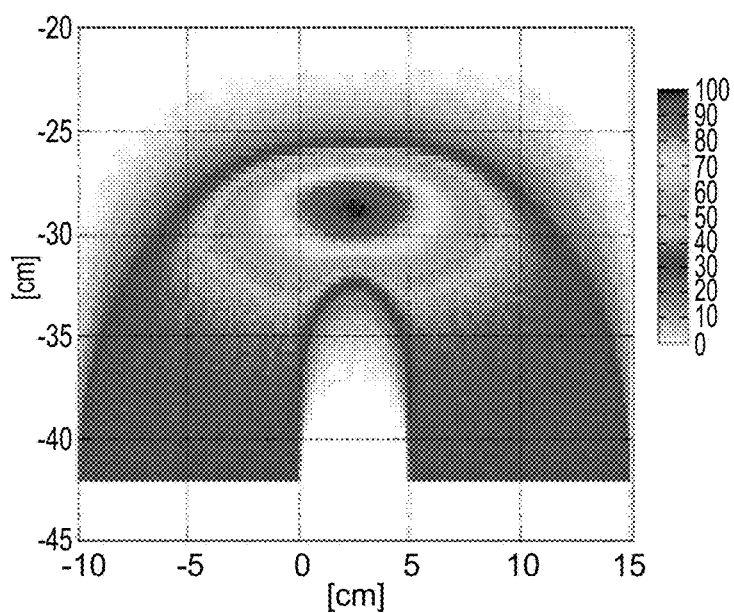

FIGS. 20A and 20B two-dimensional energy dose distributions obtained using high number of history events in the simulations software.

DESCRIPTION OF SPECIFIC EMBODIMENTS OF THE INVENTION

The present invention, in some embodiments thereof, relates to radiation therapy and, more particularly, but not exclusively, to electron radiotherapy.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

When a moving electron is subjected to a magnetic field having a component perpendicular to the electron's velocity, the motion of the electron becomes circular or at least acquires a circular component. The radius R of the motion is given by the well-known Larmor equation R=p/(eB), where p is the transverse (perpendicular) momentum of the electron with respect to the direction of the magnetic field B, and e is the charge of the electron. For example, for electron's energy of about 5 MeV, the Larmor radius is from about 3.66 cm when the magnetic field strength is about 0.5 T to about 0.31 cm when the magnetic field strength is about 6 T.

The applied transverse magnetic field produces an effective peak in the depth-dose distribution. Although originating from different physical principles, this peak is comparable to that of the Bragg Peak found in the depth-dose distribution of heavy charged particles such as protons or ions. Unlike an accelerating heavy particle proton which looses most of its energy at the end of its trajectory via the Bragg mechanism, an electron loses its energy generally in a continuous manner via multiple scatterings off Columbic fields generated by atoms in the medium.

The present inventors devised a technique which exploits the above phenomena for the purpose of treating tissue.

Reference is now made to FIG. 14 which is a schematic illustration of a radiotherapy system 10, according to some embodiments of the present invention. Radiotherapy system 10 comprises an electron beam generator 12 which generates an electron beam in the direction of a living body or an organ 24. Electron beam generators are known per se, and many types of such generators can be employed in system 10. Generator 12 may include, for example, an electron source 14 and an accelerator 16. Electron source 14 may be of any type, such as those currently employed in medical institutes or hospitals, e.g., for the purpose of producing X-ray as a result of the interaction of the electron with an X-ray target. Representative example of electron sources suitable for the present embodiments including, without limitation, the electron guns disclosed in U.S. Published Application No. 20050063514, 20050053189, and U.S. Pat. Nos. 6,282,263, 6,778,633.

Electron accelerator 16 can be an X-band accelerator, an S-band accelerator, a C-band accelerator or any other type of accelerator. Preferably, the accelerator is configured for providing the electron with kinetic energy of the order of at least 40 MeV prior to their entry into organ 24. In some embodiments, the beam is at energy of at least 40 MeV or at least 50 MeV or at least 60 MeV or 10 to 150 MeV or more.

According to some embodiments of the present invention the beam's energy is selected such that when the electrons arrive at the target location they retain sufficient residual kinetic energy. In some embodiments, the electron beam has a cross-sectional area of at least 15 or at least 20 or at least 25 or at least 30 square centimeters.

System 10 further comprises a magnetic field generator 18 which generates a magnetic field. The magnetic field serves for manipulating the electrons, optionally and preferably, at least while the electrons propagate within the tissue. Thus, in some embodiments of the present invention generator 18 is configured for generating magnetic field within organ 24. Once the magnetic field is applied, the electrons motion is confined to a limited region such as to allow them to interact with the tissue within the limited region while preventing, at partially, their interaction with tissue at depths.

Many types of magnetic field generators are contemplated. Representative examples include, without limitation, a DC driven electromagnet, an AC driven to electromagnet, a permanent magnet, a step magnet, a superconductor electromagnet and the like. An electromagnet suitable for the present embodiments includes, without limitation, a hollow coil, a coil surrounding a conductive core, a coil surrounding a magnetic core, and the like. When a AC driven electromagnet is employed, the current is optionally and preferably synchronized with the electron beam yield.

The ratio between the dose delivered to the target region and the does absorbed at the surface of the body or immediately below the surface depends on several parameters, such as the strength of the magnetic field and the cross-sectional area of the beam. In various exemplary embodiments of the invention the strength of the magnetic field and the cross-sectional area of the beam are selected sufficiently high to localize the dose at the target location.

In various exemplary embodiments of the invention system 10 comprises a controller 20 for controlling electron beam generator 12 and the magnetic field generator 18, to dynamically shift the electron beam and to dynamically redirect the magnetic field synchronously with the shift in the electron beam. It was found by the present inventors that such synchronized operation can substantially confine the electrons to a predefined volume within the tissue. For example, it was found that a symmetric profile can be obtained by an alternate shifting a beam generally parallel to itself (in a direction perpendicularly to the beam direction) and an alternate inversion of the direction of a magnetic along an axis perpendicular to both the beam direction and the direction of the shift. The combination of beam relocation and magnetic field redirection can be achieved, for example, by an alternating current wherein the current is synchronized with the pulses of electrons in the beam. A representative example of such operation is shown in the Examples section that follows.

In some embodiments of the present invention system 10 comprises a multileaf collimator 30. Collimator 30 is optionally and preferably also controlled by controller 20.

Multileaf collimators are known in the art for to produce conformal shaping of X-ray beams. A multileaf collimator includes an arrangement of a plurality of collimating leaves formed in a mutually contiguous manner. The collimating leaves are typically made of heavy metal such as tungsten. The collimating leaves perform a to function similar to that of the aperture blades. The leaves may move up and down to form a rectilinear polygonal region that is monotone to one of the axes.

A representative of multileaf collimator 30, according to some embodiments of the present invention is illustrated in FIG. 15. Multileaf collimator 30 includes a housing 32 and leaves 34 that may be adjusted along a displacement direction 33 using an adjusting mechanism (not shown). Housing 32 optionally and preferably includes the adjusting mechanism. Leaves 34 absorb electrons radiation from the electron beam emitted by generator 12. The electron beam has a main direction of propagation, which is generally defined by a center axis of the normally slightly divergent radiation beam. This main direction of propagation is illustrated as the direction 35 of radiation which in this representation points perpendicularly into the image plane. The leaves 34 may be adjusted in opposite directions to each other as far as a closed position 36, in which the distance between the front faces 37 of leaves 34 is minimal. The adjustment of leaves 34 allows an aperture to be specified for the beam passing through multileaf collimator 30 in the direction of radiation 35 so that the cross section of the radiation beam passing through corresponds to a predefined irradiation region 38 as far as edge zones 39.

Collimator 30 can be used, for example, for shifting the electron beam. According to some embodiments of the present invention multileaf collimator 30 is employed so as to open a first set of strips for a magnetic field in one direction and a second set of shifted strips for an opposed magnetic field. Such configuration can ensure a highly localized energy density at the target region.

In various exemplary embodiments of the invention the shifting and redirection is done such as to deliver a sufficiently high energy-dose to a sufficiently small internal target location 26 in body or organ 24. The energy-dose delivered to location 26 is preferably higher than the energy-dose that is delivered by the electron beam to the surface 28 of organ 24 upon entry into organ 24. Typically, but not necessarily, the energy-dose delivered to location 26 is higher from the energy-dose delivered to surface 28 by at least 50% or at least 60% or at least 70% or at least 80% or at least 90%, e.g., at least twice the energy-dose delivered to surface 28.

The internal target location 26 is typically below the surface 28 of the body or organ 24, e.g., below the skin. A typical distance between target location 26 and surface 28 is, without limitation, at least 2 cm or at least 3 cm or at least 4 cm or at least 5 cm. The volume of target location 26 is preferably, but not necessarily, at most 50 cubic centimeters or at most 40 cubic centimeters or at most 30 cubic centimeters or at most 20 cubic centimeters or at most 10 cubic centimeters.

The above numerical values can be achieved by judicious selection of the amount and direction of beam shift and field redirection. For example, the operator of system 10 can be provided with a lookup table indicating the most suitable protocol for shifting the beam and redirecting the magnetic field, for a given set of clinical parameters (amount of energy, depth and size of the target tissue). Such lookup table can be prepared in advanced, for example, using computer simulations, or using a phantom target. Also contemplated are embodiments in which the lookup table is stored in the memory of controller 20, wherein the operator feeds the set of clinical parameters, e.g., by means of a user interface 22, and controller 20 automatically selects the operation protocol and parameters based on the operator's input and the stored lookup table.

The magnetic field generated by generator 18 can have many shapes. For example, in some embodiments, a Helmholtz coil system is employed, as described, for example, in Nardi et al. (2004), supra. A Helmholtz coil system is composed of two equal and parallel current loops with current flowing in the same direction. The distance between the centers of the loops equals their radius. The magnetic field obtained by such system is approximately homogeneous with the exception of the gradient field in the region where the beam approaches the coils.

Other types of magnetic field are also contemplated. For example, in some embodiments of the present invention magnetic field generator 18 is configured for generating a multipole magnetic field.

As used herein, "a multiple magnetic field" refers to a magnetic field with more than two poles.

Representative examples of multiple magnetic fields suitable for the present embodiments including, without limitation, a quadrupole, hexapole and octupole magnetic field. For example, a quadrupole magnetic field can be generated by two dipole magnets or electromagnets located adjacent to each other in such a way that their poles are oppositely aligned. A hexapole magnetic field can be generated by a circular arrangement of magnets or electromagnets arranged such that their N-S axes are aligned radially and tangentially in an alternating manner. An octupole magnetic field can be generated by four dipole magnets or electromagnets with like pole orientation and opposite adjoining faces next to each other.

The use of multipole magnetic field is advantageous since it allows better localization of the magnetic field, and it also increases the degrees of freedom in the selection and thus allows better control over the electron beam. For example, as demonstrated in the Examples section that follows, a quadrupole magnetic field can be set to provide high concentration of energy at two small spots.

In some embodiments of the present invention magnetic field generator 18 comprises one or more coils which generate the magnetic field in response to current flowing through the turns of the coils. Alternatively or additionally, magnetic field generator 18 can include one or more magnets, such as, but not limited to, permanent magnets. The coils or magnets can be arranged in any arrangement which ensures generation of magnetic field within organ 24. FIGS. 16A-G are schematic illustrations exemplifying several coil arrangements suitable for the present embodiments.

While the embodiments below are described with a particular emphasis to coils, it is to be understood that more detailed reference to coils is not to be interpreted as limiting the scope of the invention in any way. Thus, any of the coils described below can be replaced, for example, with a permanent magnet having a cylindrical symmetry.

Figure 16A:
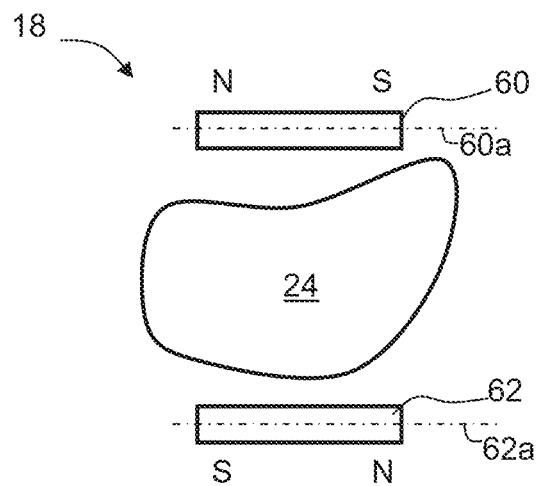

FIG. 16A illustrates a configuration in which magnetic field generator 18 comprises two coils 60 and 62 arranged at both sides of body or organ 24, such that their axes 60a and 62a do not intersect with body 24 (e.g., generally parallel to body 24). Optionally, coils 60 and 62 are arranged in an anti-parallel magnetic arrangement. Specifically the symmetry axes 60a and 62a of coils 60 and 62 are parallel to each other, but their magnetic poles (designated "N" and "S") are opposite to each other.

Figure 16B:
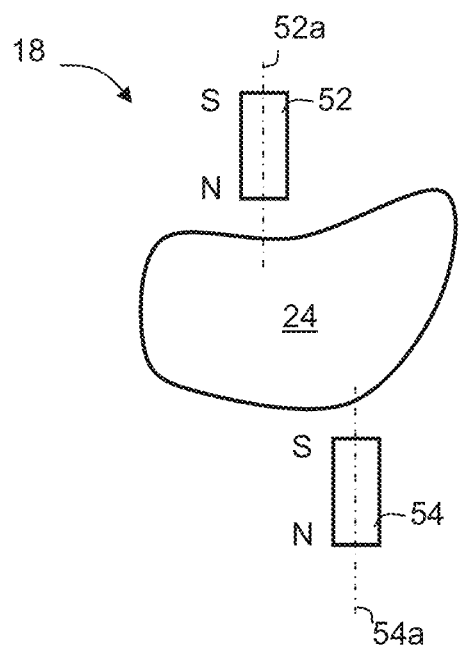

FIG. 16B illustrates a configuration in which magnetic field generator 18 comprises two coils 52 and 54 arranged at both sides of body or organ 24, such that their axes 52a and 54a intersect with body 24. Coils 52 and 54 can be arranged in a collinear arrangement having axes 52a and 54a collinear with respect to each other, or, as illustrated in FIG. 16B, axes 52a and 54a can be parallel but offset with respect to each other. Optionally, coils 52 and 54 are arranged in an opposite magnetic arrangement, with their magnetic poles (designated "N" and "S") are opposite to each other.

Figure 16C:
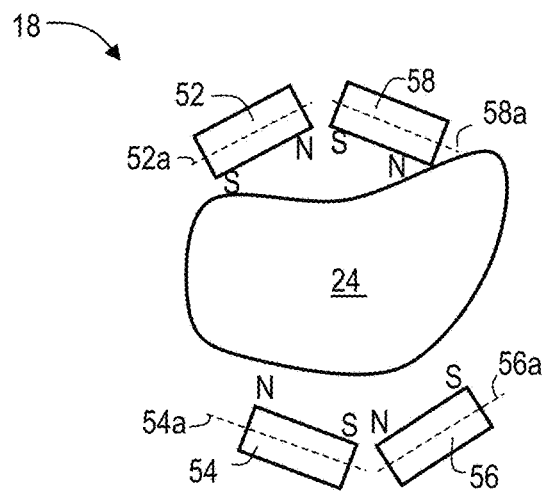
Figure 16D:
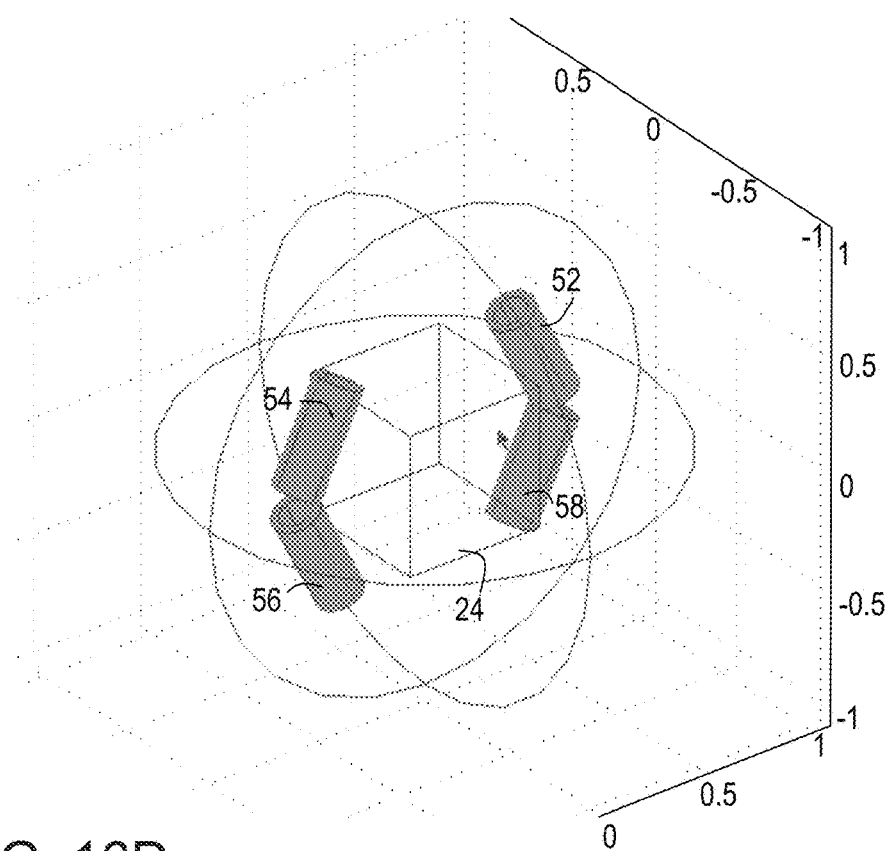

FIGS. 16C and 16D are a planar (FIG. 16C) and a perspective (FIG. 16D) illustrations of a configuration in which magnetic field generator 18 comprises four coils 52, 54, 56 and 54 arranged at both sides of body or organ 24, such that their axes 52a, 54a, 56a and 58a, respectively, are at an angle to each other. In some embodiments of the present invention, the four coils are arranged in two pairs, one at each side of body 24. Optionally, each pair of coils is arranged in a generally opposite magnetic arrangement, with their magnetic poles are opposite to each other. Optionally, the two pairs are also arranged in a generally opposite magnetic arrangement.

Figure 16E:
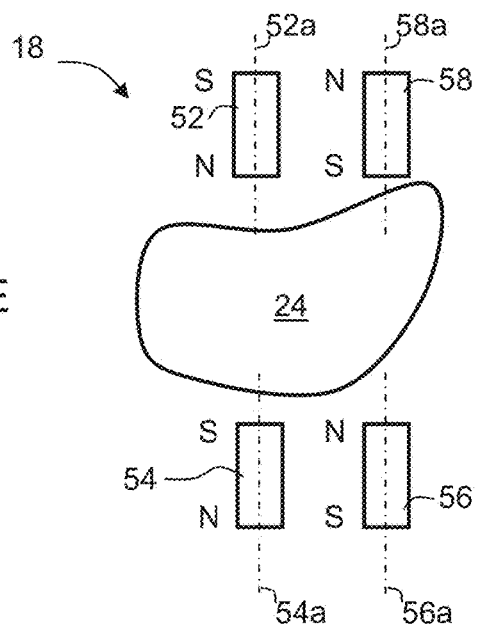

FIG. 16E illustrates a configuration in which magnetic field generator 18 comprises four coils 52, 54, 56 and 54 arranged such that their axes 52a, 54a, 56a and 58a intersect with body 24. In some embodiments of the present invention, the four coils are arranged in two pairs, one pair at each side of body 24. Shown in FIG. 16E is a configuration in which respective members of the pairs which are at both sides of body are arranged in a generally collinear arrangement with their symmetry axes collinear with respect to each other. However, this need not necessarily be the case, since, for some applications, the coils can be parallel but offset with respect to each other. Optionally, each pair of coils is arranged in an anti-parallel magnetic arrangement, with the symmetry axes parallel to each other and their magnetic poles opposite to each other. Optionally, the two pairs are also arranged in a generally opposite magnetic arrangement. As shown, respective members of the pairs which are at both sides of body 24 have their magnetic poles opposite to each other.

Figure 16F:
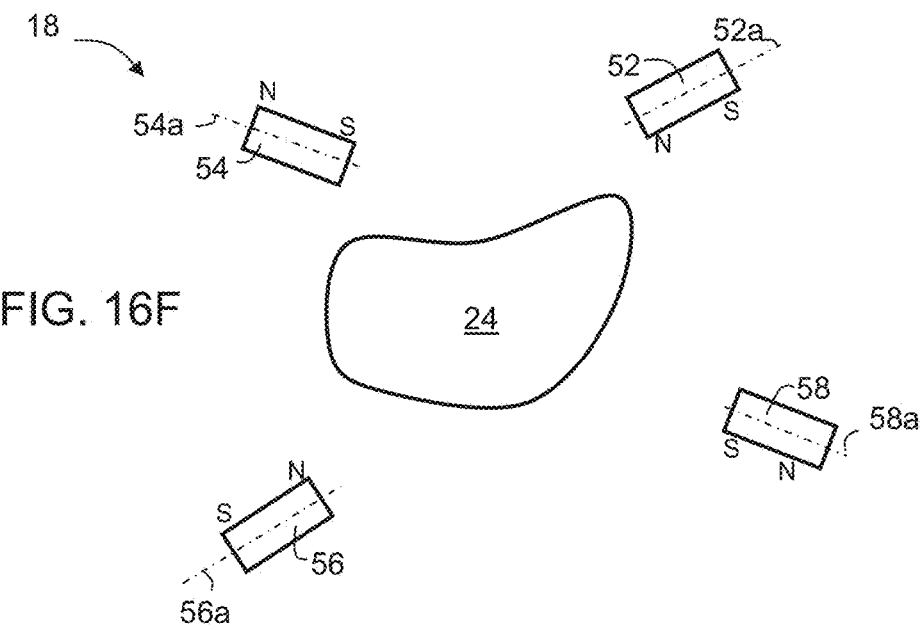

FIG. 16F illustrates a configuration in which magnetic field generator 18 comprises four coils 52, 54, 56 and 54 distributed around body 24, such that their axes 52a, 54a, 56a and 58a intersect with body 24. In some embodiments, the four coils are arranged as opposite pairs, wherein the coils of each pair are positioned at opposite sides of body 24. The axes of the coils of each pair are optionally and preferably parallel to each other. In some embodiments of the present invention, the axes of the coils of each pair are collinear. Optionally and preferably the coils of each pair are arranged in an opposite magnetic arrangement. In the representative example illustrated in FIG. 16F, the pair 54, 58 is arranged such that their south poles face body 24 and each other, while the pair 52, 56 is arranged such that their north poles face body 24 and each other.

Figure 16G:
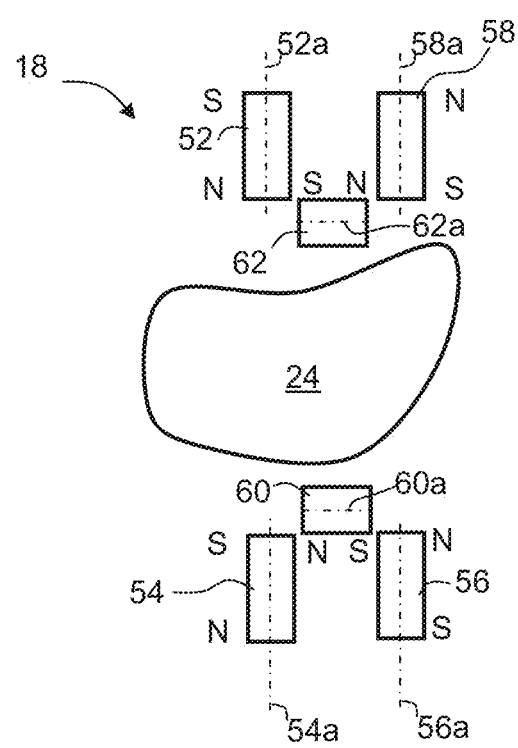

FIG. 16G illustrates a configuration in which magnetic field generator 18 comprises six coils 52, 54, 56, 54, 60 and 62. In the exemplified configuration of FIG. 16G, coils 52, 54, 56 and 58 are arranged as described above with resects to FIG. 16E, while coils 60 and 62 are arranged as described above with respect to FIG. 16A. The six coils are optionally and preferably arranged in two triplets, one triplet at each side of body. The magnetic configuration of each triplet is preferably such that the poles of coils 60 and 62 are opposite to the poles of the coils adjacent to the respective pole. Thus, each triplet has a source-sink magnetic configuration, wherein a source of magnetic field lines is adjacent to a sink of magnetic field lines. For example, in the triplet coils 52, 62 and 58, the north pole (source) intersect of coil 52 is adjacent to the south pole (sink) of coil 62, and the north pole (source) of coil 62 is adjacent to the south pole (sink) of coil 58. Similarly, in the triplet coils 54, 60 and 56, the north pole (source) intersect of coil 56 is adjacent to the south pole (sink) of coil 60, and the north pole (source) of coil 60 is adjacent to the south pole (sink) of coil 45.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics to of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Figure 1:
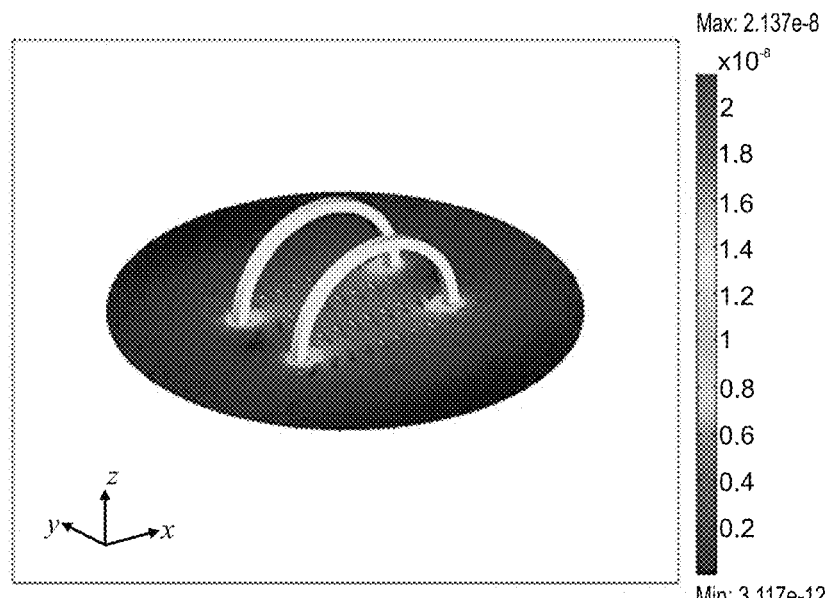

FIG. 1 shows magnetic field lines at a central cross section as generated by a Helmholtz coil system. The electron beam is generally along the z direction and the magnetic field on the x-y plane is generally along the y direction. The magnetic field lines were obtained by computer simulations using the FLUKA software [Battistoni et al., Proceedings of the Hadronic Shower Simulation Workshop 2006, M. Albrow, R. Raja eds., AIP Conference Proceeding 896, 31-49, (2007); Fasso' et al. CERN-2005-10 (2005), INFN/TC_05/11, SLAC-R-773].

The transport of electrons and photons was calculated by activating the electromagnetic FLUKA (EMF) routine and using the Moliére multiple coulomb scattering theorem. The calculations took into account the effects of the magnetic field on the motion of the electron or photon as well as other considerations such as deviations and shifts with respect to the initial free path of the particle, path length corrections, effects of boundary crossing on the path, and the like.

Figure 2:
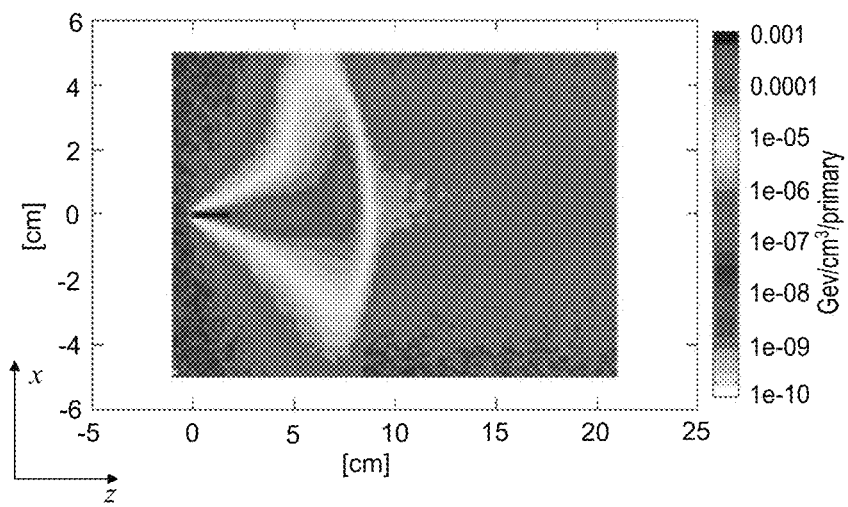

Simulations have also been conducted for step-function magnetic field, such as the magnetic field described in Nardi and Barnea (1999) supra. FIG. 2 shows results of such simulations for a 25 MeV electron beam entering perpendicularly to a tissue-simulating medium. The simulated magnetic had a step-function spatial behavior selected such that the field strength was 3 T at tissue depths above 4 cm and 0 otherwise. Shown in FIG. 2 are energy dose expressed as a ratio relative to the energy of the primary beam as a function of the depth within the tissue along the z direction.

Additional simulations were performed using an EGS5 code system [Hirayama, H., Y. Namito, A. F. Bielaje, S. J. Wilderman, and W. R. Nelson. 2005. The EGS5 Code System. SLAC-R-730 and KEK Report 2005-8].

Figure 3:
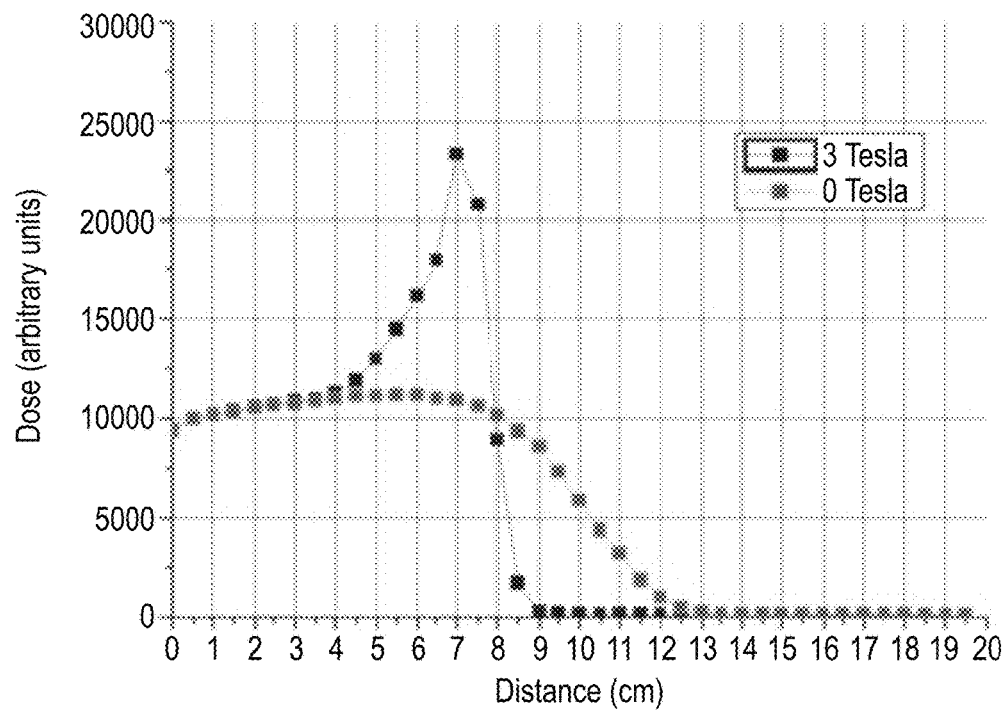

FIG. 3 shows the results of such simulation using the same parameters as described above (25 MeV electron beam, step-function 3 T magnetic field). The curves in FIG. 3 show the energy deposition in arbitrary units as a function of the depth in centimeters.

Figure 4:
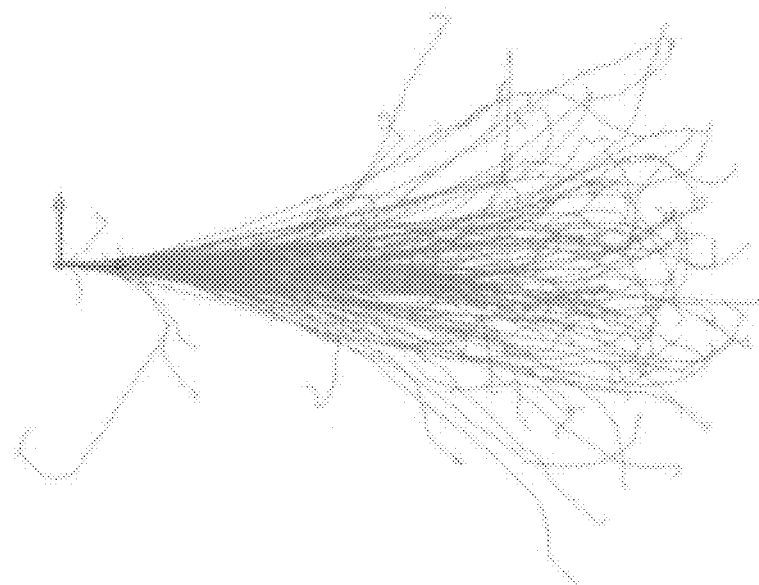
Figure 5:
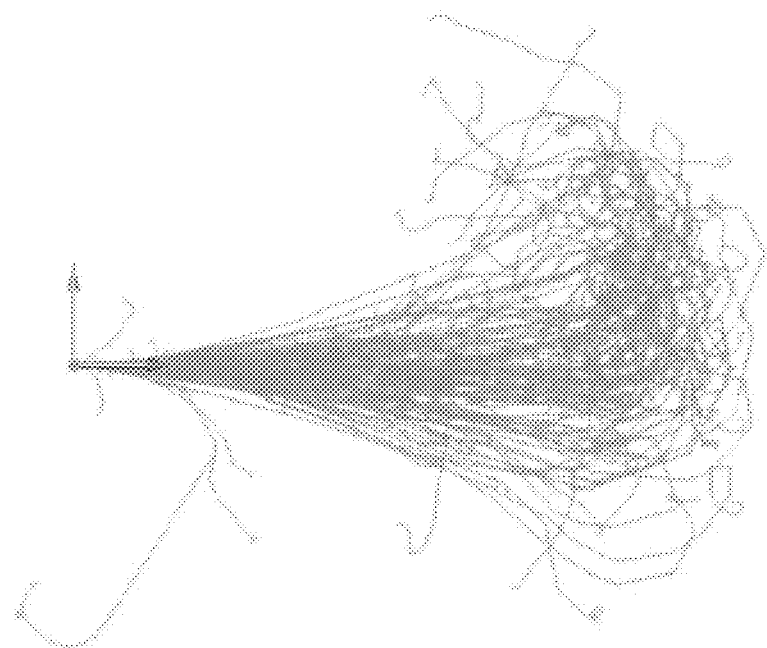

The electron trajectories with and without application of magnetic field having a step-function spatial dependence are shown in FIG. 4 (without magnetic field) and FIG. 5 (with magnetic field). The trajectories were obtained by the Simple Geo program [Theis et al., "Interactive three dimensional visualization and creation of geometries for Monte Carlo calculations," (2006) Nuclear Instruments and Methods in Physics Research A 562, pp. 827-829. As shown, the magnetic field successfully enhances the concentration of electrons at a depth of 7 cm.

Figure 6A:
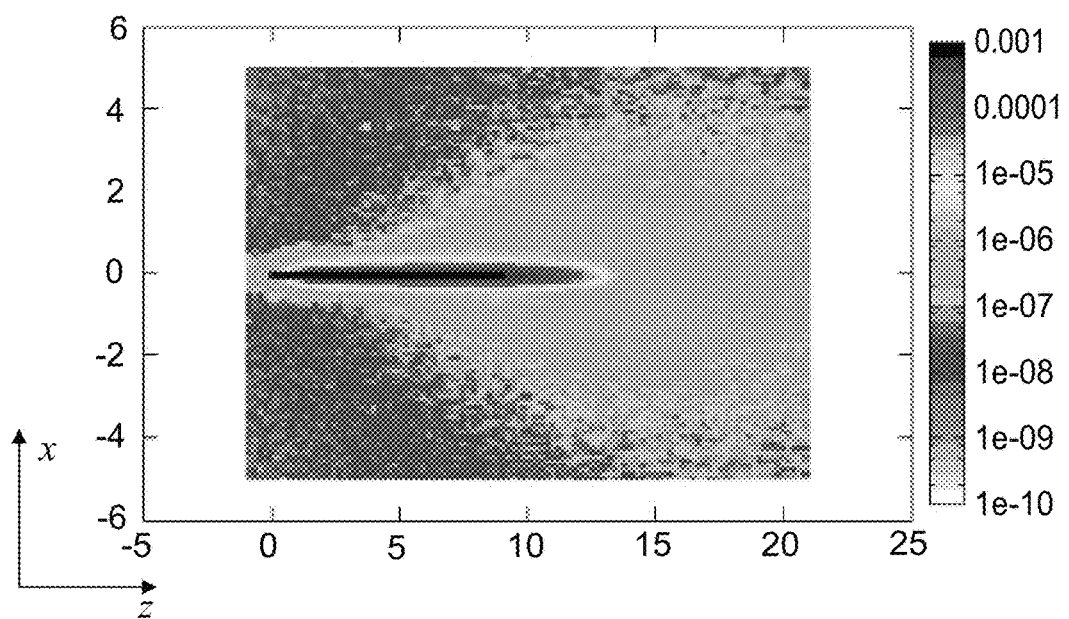
Figure 6B:
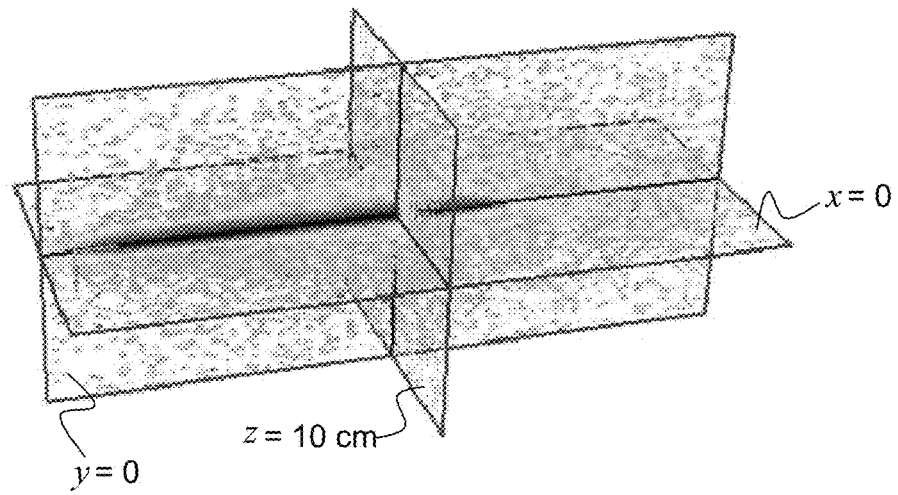

Further simulations were performed for a longitudinal magnetic field wherein the magnetic field is collinear with the electron beam. The simulations were performed by the FLUKA Monte Carlo transport simulation as described above for a 25 MeV electron beam and a 20 T longitudinal magnetic field. The results are shown in FIGS. 6A and 6B, where FIG. 6A shows the energy dose as a function of the depth in the x-z plane (z is the direction of the electron beam), and FIG. 6A shows the energy dose distribution over three planar cuts (i) y=0, (ii) x=0, and (iii) z=10 cm. As shown the longitudinal magnetic field reduces the penombra of the beam.

Figure 7:
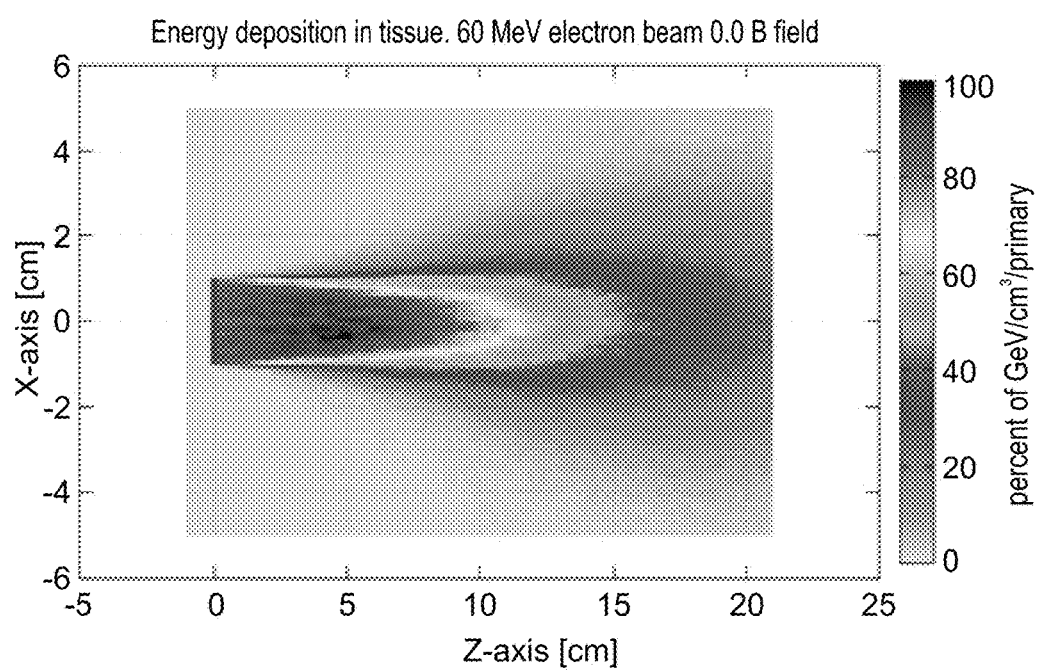

FIG. 7 shows results of computer simulations performed in accordance with some embodiments of the present invention for a 60 MeV parallel electron beam having, on entry, a square cross-sectional area of 1 $cm^2$, in the absence of magnetic field. The simulations were performed using the FLUKA software as described above. Shown in FIG. 7 an absorption map in the x-z plane where the energy dose is expressed in percentage. As shown an effective amount of about 20 $GeV/cm^3$ is delivered to depths of 15-20 cm.

Figure 8:
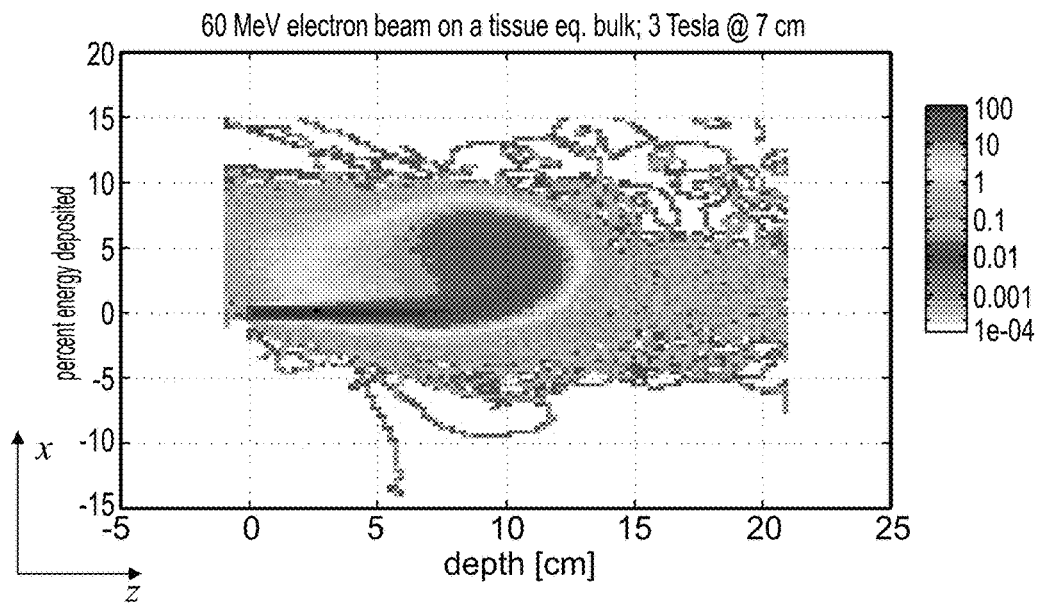

FIG. 8 shows results of computer simulations performed in accordance with some embodiments of the present invention for a 60 MeV electron beam in the presence of a 3 T magnetic field directed along the y direction at z≥7 cm. The simulation were performed using the FLUKA software as described above. Shown in FIG. 8 is an absorption map in the x-z plane, where the energy dose is expressed in percentage of to the maximal energy. As shown, the magnetic field successfully concentrates about 70% of the energy at depths of 7-12 cm.

Figure 9C:
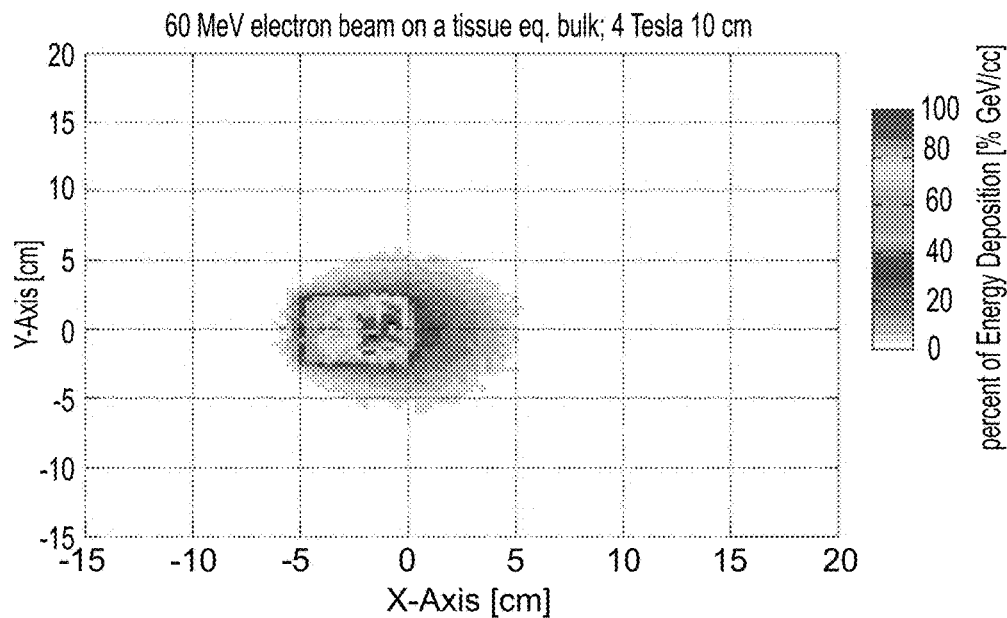

FIGS. 9A, 9B and 9C show results of computer simulations performed in accordance with some embodiments of the present invention for a 60 MeV electron beam having, on entry, a square cross-sectional area of 25 cm², the presence of a 4 T magnetic field directed along the x direction at z≥10 cm. The simulations were performed using the USRBIN routine of the FLUKA software which quantifies the energy density (energy per unit volume). Since the electron energy was high, the stopping power was not neglected.

FIGS. 9A and 9B show the results of simulation having 100,000 particle tracking histories. A typical energy density which was obtained was about $5.5 \times 10^{-5}$ GeV/cm³ per a single tracking history. An absorption map in percentage is presented in the y-z plane, using a logarithmic (FIG. 9A) and a linear (FIG. 9B) scale. As shown, about 90% of the absorbed energy is concentrated at depths of 11-13 cm. FIG. 9C shows the absorption map in the x-y plane at z=10 cm.

The present embodiments contemplate manipulation of electron beam by combination of dynamic beam relocation and magnetic field redirection. A representative example of such procedure is depicted in FIGS. 10A-D.

FIG. 10A show simulation results of a beam similar to the beam discussed above with respect to FIGS. 9B and 9C, except that the beam is shifted 5 cm in the x direction and the magnetic field direction is inverted (−y direction).

FIGS. 10B-D show the results of simulations which combine the simulations shown in FIGS. 9B and 10A. An absorption map in percentage is presented in the x-z plane (FIG. 10B) y-z plane (FIG. 10C) and x-y plane (FIG. 10D). As shown, a substantially symmetric profile is obtained, with about 90% of the absorbed energy concentrated at depths of 11-13 cm and substantially low doses at other depths.

The combination of beam relocation and magnetic field redirection can be achieved, for example, by an alternating current wherein the current is synchronized with the pulses of electrons in the beam.

FIG. 11 is a graph describing the ratio of the maximal dose which is delivered with application of magnetic field to the maximal dose which is delivered in the absence of magnetic field. The graph shows the ratio as a function of the depth for three magnetic field strengths (3 T, 4 T and 5 T). As shown, for higher magnetic field strengths the ratio at a given depth is higher.

FIGS. 12A-C show simulation results for a 60 MeV two opposed electron beams with a magnetic field of 4 T at a target region located at a depth z of 10 cm. The field lines of the magnetic field at the target region were directed along the −x, +x, −y and +y directions. The simulations were performed using the FLUKA software as described above. FIG. 12A shows an absorption map in percentage in the x-z plane, FIG. 12B shows an absorption map in percentage in the y-z plane, and FIG. 12C is a graph showing the energy dose in percentage as a function of the depth z. As shown, the does is highly localized and symmetric at the target region.

FIGS. 13A-D show simulation results for a 60 MeV parallel electron beam propagating from z=−20 cm along the z direction and having, on entry, a square cross-sectional area of 40 cm². A quadrupole magnetic field of 3.5 T is applied at a target region located from z=−20 cm to z=+20 cm. The quadrupole magnetic field was simulated as if it was generated by 4 coils, similarly to the fields employed in synchrotrons to maintain the particles in a storage ring. The simulations were performed using the COMSOL™ software.

Figure 13A:
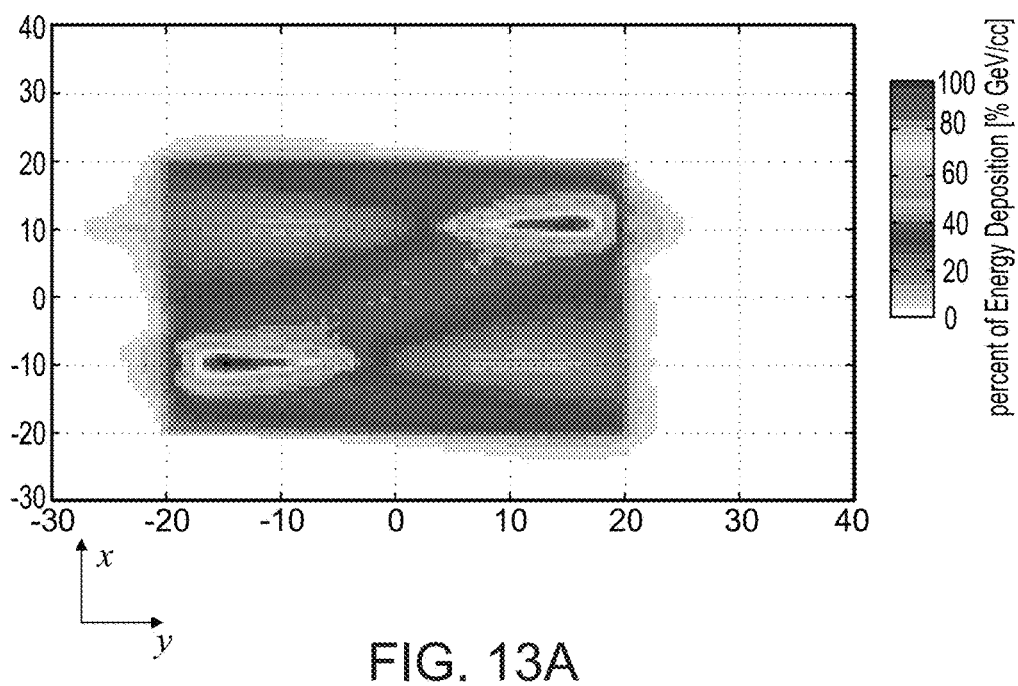
Figure 13B:
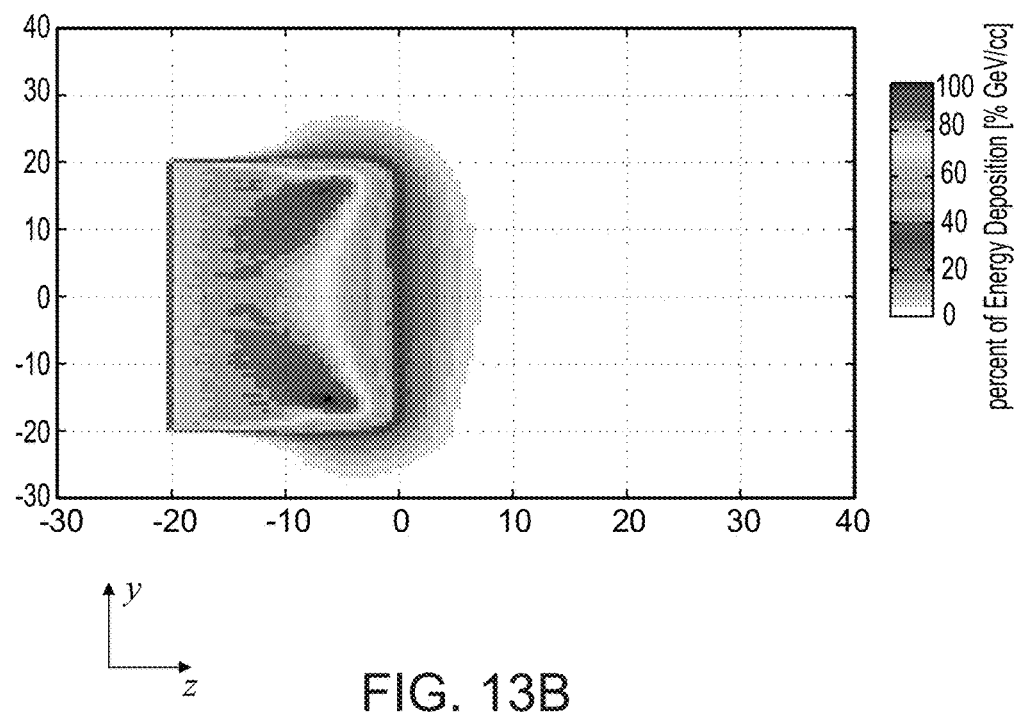
Figure 13C:
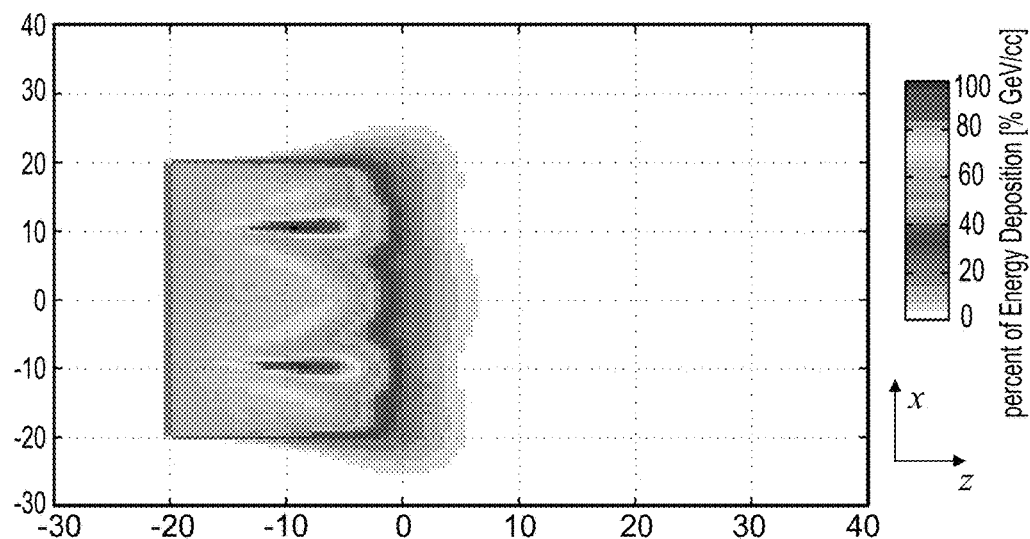
Figure 13D:
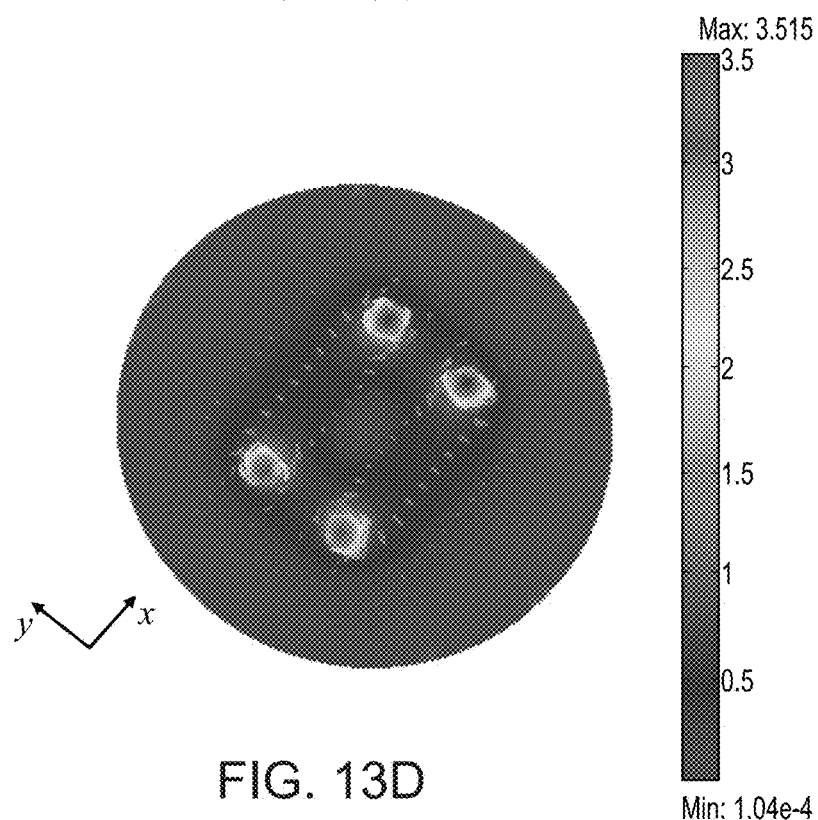

FIG. 13A shows an absorption map in percentage in the x-y plane, FIG. 13B shows an absorption map in percentage in the y-z plane, and FIG. 13C shows an absorption map in percentage in the x-z plane. The quadrupole magnetic field lines are shown in FIG. 13D.

Several additional configurations for the magnetic field generator suitable for some embodiments of the present invention are shown in FIGS. 17A-F.

FIG. 17A shows magnetic field vectors for a configuration similar to the two-coil configuration illustrated in FIG. 16A. The cylinders represent the coils and the arrowheads represent the magnetic field vectors. FIG. 17B shows magnetic field vectors and intensity in normalized units for a configuration similar to the two-coil configuration illustrated in FIG. 16B. The square centered at coordinate (0,0) represent the body or organ, and the rectangles at both sides of the square represent the coils. FIG. 17C shows magnetic field vectors and intensity in normalized units for a configuration similar to the illustration in FIG. 16E. FIG. 17D shows magnetic field vectors and intensity in normalized units for a configuration similar to the four-coil configuration illustrated in FIG. 16F. FIGS. 17E and 17F show magnetic field vectors (FIG. 17E) and intensity in normalized units (FIG. 17F) for a configuration similar to the four-coil configuration illustrated in FIG. 16G.

Computer simulations were performed for magnetic field generated by six coils, arranged in the configuration shown in FIGS. 17E and 17F. The simulations were performed for electron beams of various shapes and energies.

The results of the simulations are shown in FIGS. 18A-H, 19A-H and 20A-B, where FIGS. 18A-F show the maximal energy in percentage as a function of the depth, and FIGS. 19A-F and 20A-D show two-dimensional energy dose distributions.

The results are presented for: a 75 MeV electron beam having, on entry, a square cross-sectional area of 5×5 cm² (FIGS. 18A and 19A); a 75 MeV electron beam having, on entry, a square cross-sectional area of 3×3 cm² (FIG. 18B), a 75 MeV electron beam having, on entry, a square cross-sectional area of 2×6 cm² (FIG. 18G), a 100 MeV electron beam having, on entry, a square cross-sectional area of 5×5 cm² (FIGS. 18C and 19C); a 100 MeV electron beam having, on entry, a rectangular cross-sectional area of 2×6 cm² (FIGS. 18D and 19B); a 100 MeV electron beam having, on entry, a square cross-sectional area of 3×3 cm² (FIG. 18H); a 150 MeV electron beam having, on entry, a square cross-sectional area of 5×5 cm² (FIG. 19D); a 60 MeV electron beam having, on entry, a square cross-sectional area of 5×5 cm² (FIGS. 18E, 19E and 19F); and a 60 MeV electron beam having, on entry, an annular cross-section (FIGS. 18F, 19G, 19H and 20A-B). FIGS. 20A and 20B, are similar to FIGS. 19G and 19H, except that FIGS. 20A and 20B where obtained using higher number of history events in the FLUKA software.

FIGS. 18A to 20B, demonstrate the ability of the technique of the present embodiments to localize the energy so as to deliver a sufficiently high energy-dose to a sufficiently small internal target location.

Following is a representative example of a coil, suitable for use as a component in the magnetic field generator of the present embodiments. The calculations presented below are for a coil having a 60 mm radius core made of steel 1006, wherein the thickness of the coil surrounding the core is 43.12 mm and the height of the coil is 323.44 mm. It is to be understood that these parameters are not to be considered as limiting the scope of the present invention in any way. Table 1 below summarize the characteristics and properties of the coil.

TABLE 1

| | |
|---|---|
| wire type | 12AWG |
| wire core diameter | 2.053 mm |
| wire insulation thickness | 0.02032 |
| wire total diameter | 2.07332 |
| number of layers | 20 |
| number of turns per layer | 150 |
| total number of turns | 3000 |
| current | 2.5 A |
| current times the total number of turns | 7500 A |
| wire cross section | 3.3103 mm$^2$ |
| area per unit current | 0.7552 mm$^2$/A |
| coil surface area for heat dissipation | 0.2166 m$^2$ |
| maximal radius of the coil | 0.103 m |
| radius of core | 0.06 m |
| average radius of the coil | 0.0816 m |
| coil perimeter | 0.648 |
| average length of one turn | 0.5125 |
| total length of wire | 1537.4174 |
| expected resistivity | 8.3598 |
| expected voltage | 20.8995 V |
| dissipation | 52.2488 W |
| expected raising temperature | 34.4592° C. |
| operation temperature, assuming starting temperature 30° C. | 64.4592° C. |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A radiotherapy system, comprising:
an electron beam generator, for generating an electron beam, at an energy of at least 60 MeV, directed to a surface of a living body to propagate in said living body;
at least two coils, for generating a multipole magnetic field within said living body; and
a controller having a circuit configured for controlling said at least two coils to generate and to dynamically redirect the multipole magnetic field, by applying an alternating current to the at least two coils; the multipole magnetic field concentrates said electron beam while electrons of said beam propagate in said living body, and wherein the controller having the circuit is configured for controlling said electron beam generator to dynamically shift said electron beam;
wherein said shifting of the electron beam with the electron beam generator and said redirecting of the magnetic field with the at least two coils occurs synchronously and results in the delivery of an energy-dose into said living body with an energy-dose peak at an internal target location which is at a depth of at least 7 cm in said living body;
wherein said controller is configured to control said electron beam and said at least two coils such that said energy-dose has a symmetric profile with respect to each of an x, y and z axis.

2. The system according to claim 1, further comprising a multileaf collimator for establishing said shifting.

3. The system according to claim 1, wherein said multipole magnetic field is selected from the group consisting of a quadrupole magnetic field, a hexapole magnetic field and an octupole magnetic field.

4. The system according to claim 1, wherein said energy-dose is higher by at least 50 percent from an energy-dose delivered by said beam to a surface of said living body upon entry thereto.

5. The system according to claim 1, wherein said target location is located at least 12 centimeters below a surface of said living body.

6. The system according to claim 1, wherein said target location is at most 50 cubic centimeters.

7. The system according to claim 1, wherein said beam has a cross-sectional area of at least 15 square centimeters.

8. The system according to claim 1, wherein said at least two coils have a symmetry axis arranged to receive a living body therebetween such that symmetry axes of said coils do not intersect with said body.

9. The system according to claim 1, wherein said at least two coils have a symmetry axis arranged to receive a living body therebetween such that symmetry axes of said coils intersect with said body.

10. The system according to claim 1, wherein said at least two coil comprise four coils or magnets having a symmetry axis arranged to receive a living body such that a first pair of coils or magnets is at one side of said body and a second pair of coils or magnets is at an opposite side of said body, and wherein symmetry axes of said coils or magnets are at an angle to each other.

11. The system according to claim 1, wherein said at least two coils comprise four coils or magnets having a symmetry axis arranged to receive a living body such that a first pair of coils or magnets is at one side of said body and a second pair of coils or magnets is at an opposite side of said body, and wherein symmetry axes of said coils or magnets intersect with said body.

12. The system according to claim 1, wherein said at least two coils comprise four coils or magnets having a symmetry axis arranged to receive a living body such that said coils or magnets are distributed around said body, wherein symmetry axes of said coils or magnets intersect with said body.

13. The system according to claim 1, wherein said at least two coils comprise six coils or magnets having a symmetry axis arranged to receive a living body such that a first triplet of coils or magnets is at one side of said body and a second triplet of coils or magnets is at an opposite side of said body, and wherein for each triplet, a symmetry axis of a middle coil or magnet of said triplet is generally orthogonal to symmetry axes of the other two coils or magnets of said triplet.

14. A method of radiotherapy, comprising operating the system according to claim 1, so as to deliver an effective amount of damaging radiation to an internal target tissue in a living body.

15. The system according to claim 1, wherein said controller is configured to effect an alternate shifting of said beam generally parallel to itself and an alternate inversion of a direction of said magnetic field along an axis generally perpendicular to both the beam direction and the direction of the shift.

16. The system according to claim 1, wherein said controller is configured for controlling said electron beam and said at least two coils using alternating current that is synchronized with pulses of electrons in said electron beam.

17. A method of radiotherapy, comprising:
- generating an electron beam from an electron beam generator;
- directing the electron beam at an energy of at least 60 MeV to a surface of a living body to propagate in said living body;
- generating, with at least two coils, a multipole magnetic field within said living body, while electrons of said beam propagate within said living body;
- controlling said at least two coils to concentrate said electron beam by applying an alternating current to said at least two coils; wherein the alternating current is synchronized with a plurality of pulses of electrons in said electron beam; and
- dynamically shifting said electron beam with the electron beam generator and, synchronously with said shifting, dynamically redirecting said magnetic field with the at least two coils;
- wherein said shifting said electron beam and said redirecting said magnetic field results in the delivery of an energy-dose having a symmetric profile with respect to each of an x, y and z axis into said living body with an energy-dose peak at an internal target location which is at a depth of at least 7 cm in said living body.

18. The method according to claim 17, wherein said shifting is by a multileaf collimator.

19. The method according to claim 17, wherein at least one of strength of said magnetic field, a cross-sectional area of said beam, an extent and rate of said shifting, and an extent and rate of said redirecting is selected such as to deliver an energy-dose to an internal target location in a living body.

* * * * *